United States Patent
Takai et al.

(10) Patent No.: US 9,446,900 B2
(45) Date of Patent: Sep. 20, 2016

(54) TUBE SORTER AND TUBE SORTING SYSTEM

(71) Applicant: SYSMEX CORPORATION, Kobe-shi, Hyogo (JP)

(72) Inventors: Kei Takai, Kobe (JP); Nobuyoshi Yamakawa, Kobe (JP); Hiroo Tatsutani, Kobe (JP); Yuji Takano, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 88 days.

(21) Appl. No.: 14/168,664

(22) Filed: Jan. 30, 2014

(65) Prior Publication Data

US 2014/0212248 A1  Jul. 31, 2014

(30) Foreign Application Priority Data

Jan. 31, 2013 (JP) ................................ 2013-016553
Jan. 31, 2013 (JP) ................................ 2013-016556
Sep. 30, 2013 (JP) ................................ 2013-205519

(51) Int. Cl.
*G01N 35/04* (2006.01)
*B65G 1/06* (2006.01)

(52) U.S. Cl.
CPC ................ *B65G 1/06* (2013.01); *G01N 35/04* (2013.01)

(58) Field of Classification Search
None
See application file for complete search history.

(56) References Cited

U.S. PATENT DOCUMENTS

| 5,009,316 | A | * | 4/1991 | Klein | ........................ B01L 9/06 206/443 |
| 5,351,801 | A | * | 10/1994 | Markin | .................. B65G 37/02 198/346.1 |
| 6,255,614 | B1 | | 7/2001 | Yamakawa et al. | |
| 7,360,984 | B1 | * | 4/2008 | Sugiyama | ............... B01L 9/543 414/798.1 |
| 2013/0142596 | A1 | * | 6/2013 | Murakami | ............. B65G 49/00 414/222.01 |

FOREIGN PATENT DOCUMENTS

| CN | 1333730 A | | 1/2002 |
| JP | 4009668 | * | 1/1992 |
| JP | H09-251024 A | | 9/1997 |
| JP | 2002-040034 A | | 2/2002 |
| JP | 2007-322287 A | | 12/2007 |

OTHER PUBLICATIONS

Translation of JP4009668, originally published Jan. 14, 1992.*

* cited by examiner

*Primary Examiner* — Michael McCullough
*Assistant Examiner* — Mark Hageman
(74) *Attorney, Agent, or Firm* — Mots Law, PLLC

(57) ABSTRACT

Disclosed is a tube sorter comprising: a transporting section configured to transport a sample rack; a storage arranged at a higher level than the transporting section, capable of storing a plurality of sample tubes; a lifting section configured to lift up the sample rack transported by the rack transporting section; and a sample tube transferring section configured to remove a sample tube from the sample rack lifted up by the lifting section and set the removed sample tube in the storage.

19 Claims, 24 Drawing Sheets

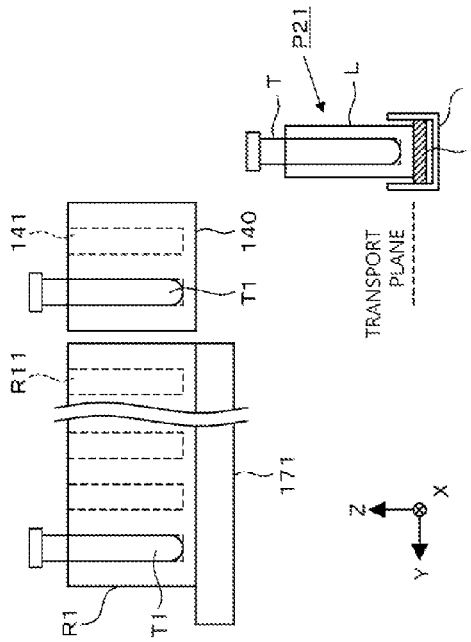
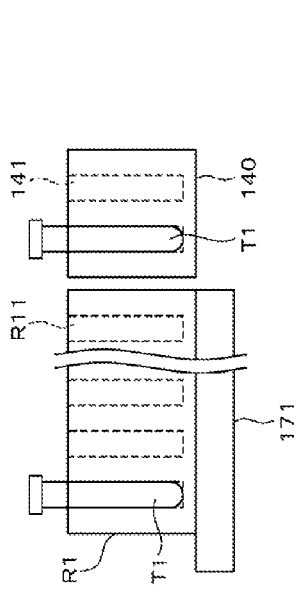
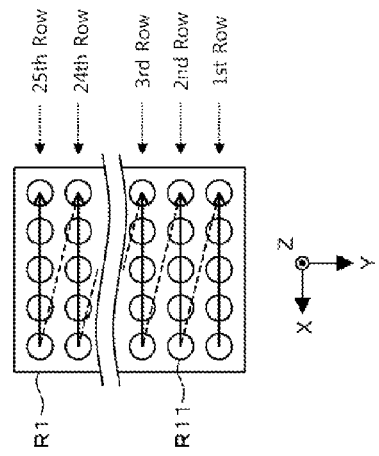
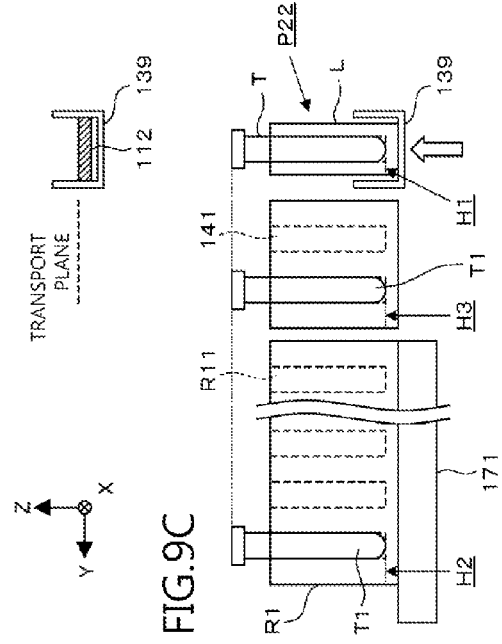

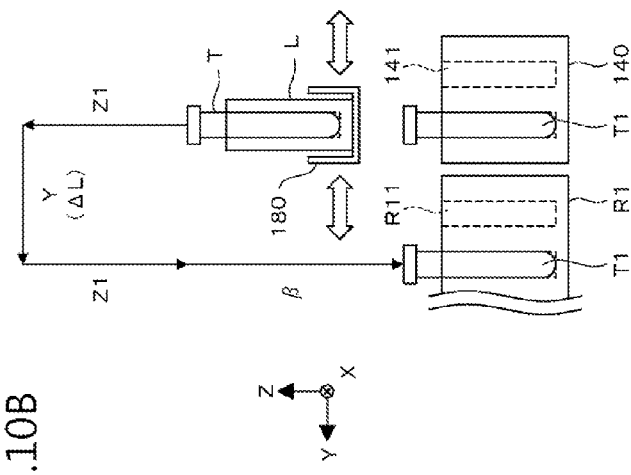
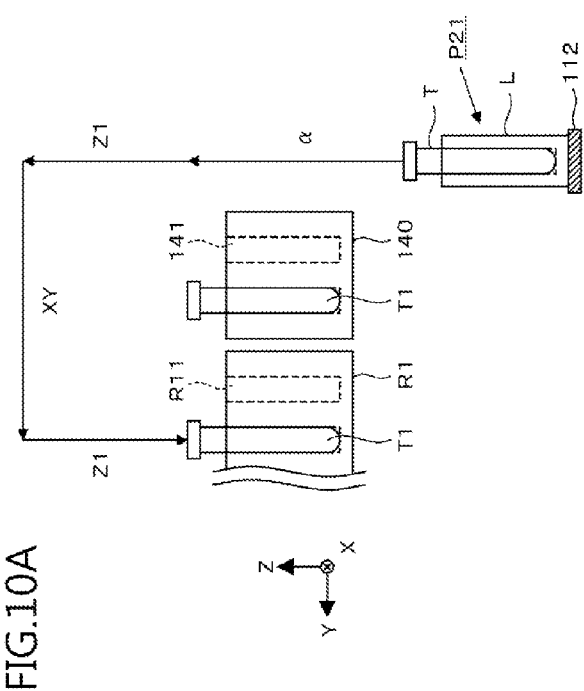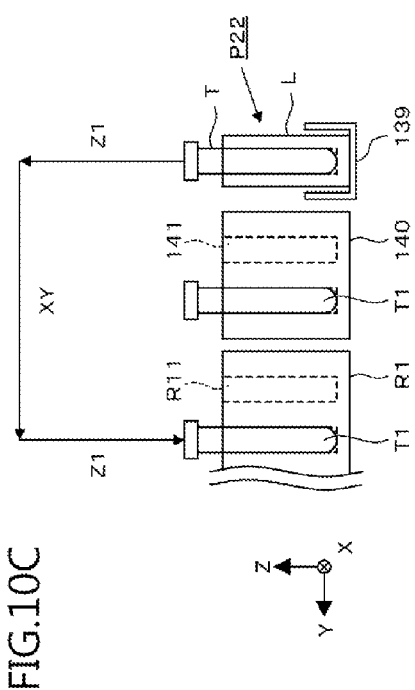

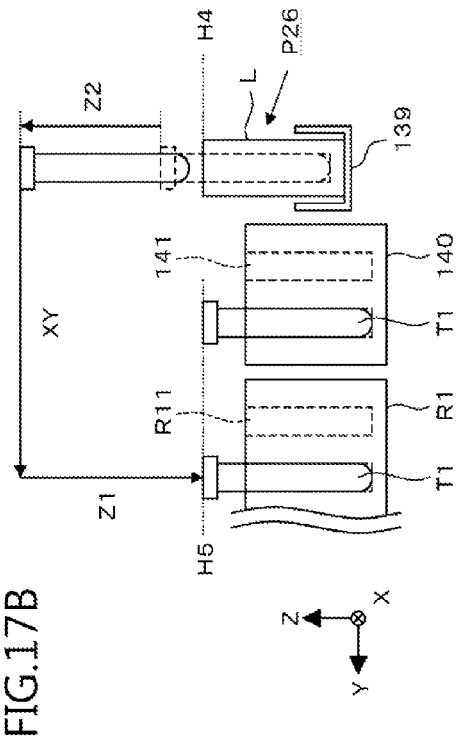
FIG.17A
FIG.17B
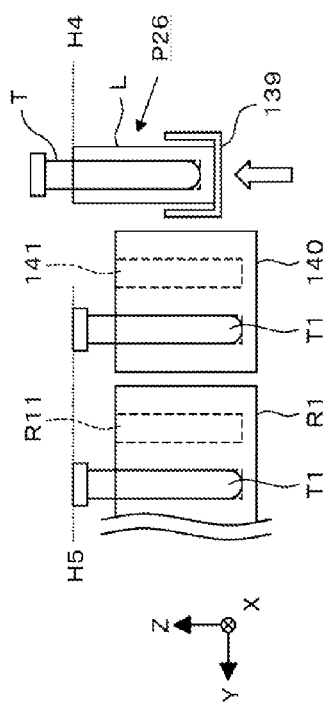
FIG.17C

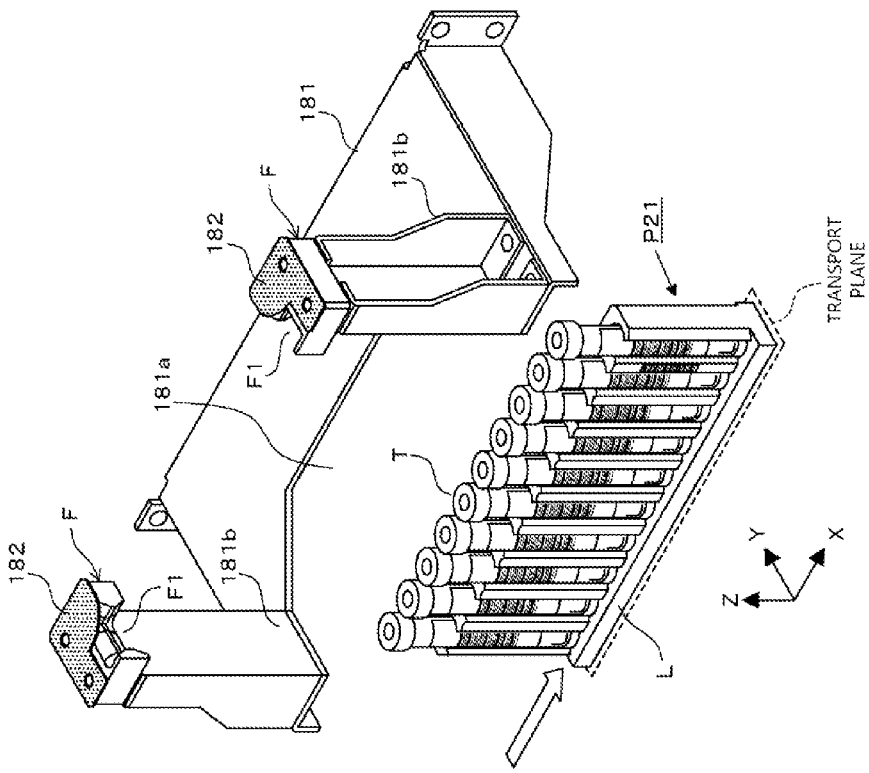
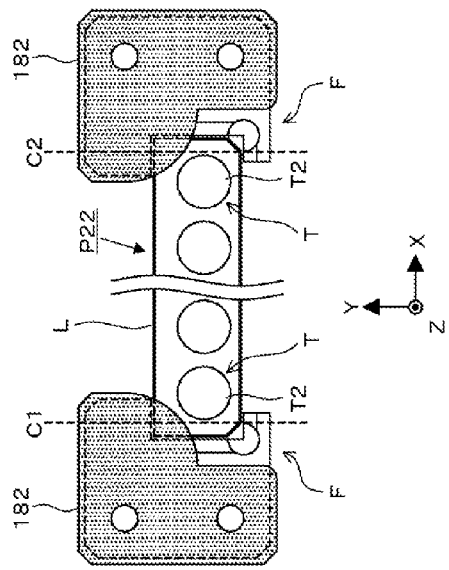
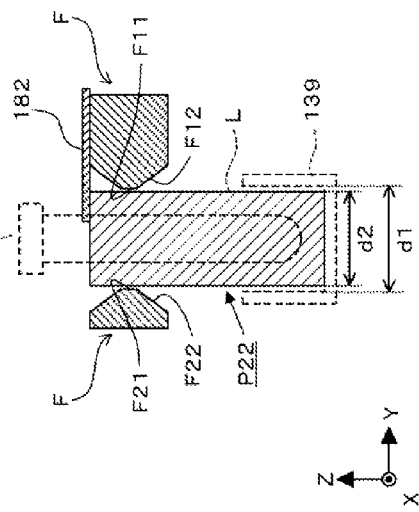
FIG.24A
FIG.24B
FIG.24C

TUBE SORTER AND TUBE SORTING SYSTEM

FIELD OF THE INVENTION

The present invention relates to a tube sorter capable of transferring sample tube containing sample from one sample rack to another sample rack. The present invention further relates to a tube sorting system.

BACKGROUND

There are known sample processing systems for processing samples such as blood and urine. In this type of sample processing system, a sample contained in a sample tube is transported to a sample processing apparatus by, for example, a transporting device transporting a sample rack which holds the sample tube.

In sample processing systems which transport sample tubes via sample racks, a tube sorter is used to automatically sort the sample tubes for each type of process into predetermined sample racks prior to the sample processes for processing efficiency relative to the plurality of samples (for example, Japanese Laid-Open Patent Application No. 2002-40034). In the sample sorter disclosed in Japanese Laid-Open Patent Application No. 2002-40034, the rack is transported to the sample sorting position by the sample tube transporting means. Thereafter, the sample tube is removed from the rack by a robot hand, and the removed sample tube is transferred to the sorting destination.

In the sample sorter disclosed in Japanese Laid-Open Patent Application No. 2002-40034, although the transport line of the sample racks is behind the sorting destination rack, the transport line is preferably arranged in front of the destination rack with sorted sample tubes and removed from the front side of the apparatus. However, the transport line must be stopped while removing the sorted sample tubes due to obstruction of the sample rack passing through the transport line in this configuration.

There is also a problem such, in the sample sorter disclosed in Japanese Laid-Open Patent Application No. 2002-40034, the order of transporting racks cannot be substituted.

SUMMARY OF THE INVENTION

A summary of the present invention is below. It is to be noted that the scope of the present invention is defined solely by the appended claims, and is not affected to any degree by the statements within this summary.

A first aspect of the present invention is a tube sorter comprising: a transporting section configured to transport a sample rack; a storage arranged at a higher level than the transporting section, capable of storing a plurality of sample tubes; a lifting section configured to lift up the sample rack transported by the rack transporting section; and a sample tube transferring section configured to remove a sample tube from the sample rack lifted up by the lifting section and set the removed sample tube in the storage.

A second aspect of the present invention is a tube sorter comprising: a transporting section configured to transport a sample rack along a transporting path; a lifting section configured to lift the sample rack up at a predetermined position on the way of the transporting path; a storage arranged at a higher level than the transporting section, capable of storing a plurality of sample tubes; a tube transferring section configured to transfer a sample tube between the storage and the sample rack lifted up by the lifting section; wherein the rack transporting section is configured to transport a sample rack to pass through the predetermined position beneath another sample rack while the lifting section is lifting it up.

A third aspect of the present invention is a tube sorting system comprising: the tube sorter of the first aspect as a first tube sorter; a second tube sorter arranged adjacently to the first tube sorter, the second tube sorter comprising at least: a transporting section configured to transport a sample rack delivered from the first tube sorter; a storage capable of storing a plurality of sample tubes; and a sample tube transferring section configured to remove a sample tube from the sample rack and set the removed sample tube in the storage; and a controller programmed to control the first tube sorter to pass through a first sample rack by the transporting section while the lifting section of the first tube sorter is lifting a second sample rack and to deliver the first sample rack to the second tube sorter.

BRIEF DESCRIPTION OF THE DRAWINGS

FIGS. 9A through 9D show the sample tube transfer sequence;

FIGS. 10A through 10C show the movement distance of the sample tube when the tube is transferred;

FIGS. 17A and 17B show the movement distance of the sample tube when the tube is transferred in a modification;

FIG. 17C is a schematic view showing the structure when viewing the transporting section from the front;

FIGS. 24A through 24C show modifications using a flat spring as the rack regulating member.

EMBODIMENT

A sample processing system for examining and analyzing blood is offered as an example of an embodiment of the present invention. This embodiment is described below with reference to the drawings.

Figure 1:
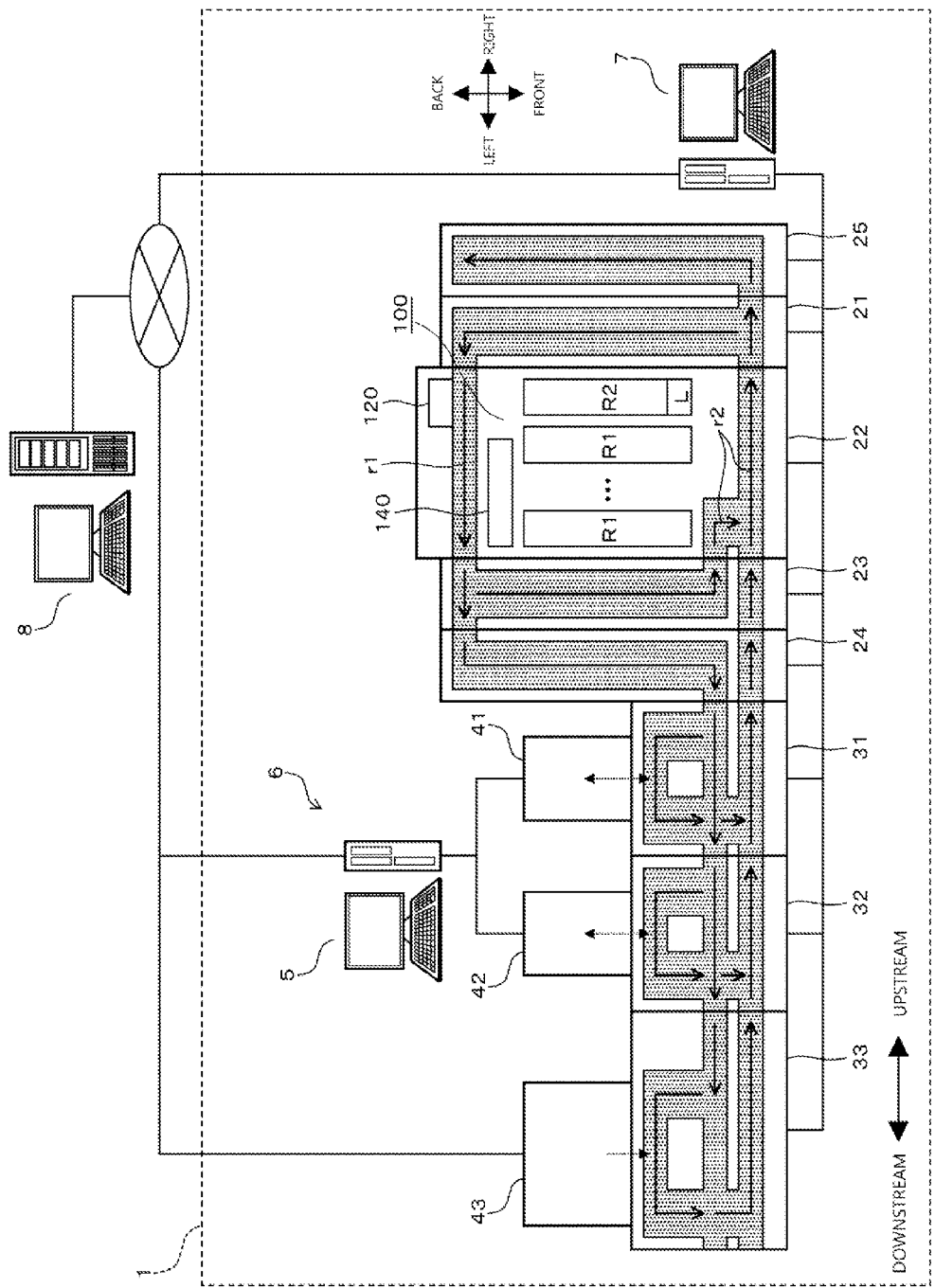
FIG. 1 shows the structure of the sample processing system viewed from above.

FIG. 1 shows the structure of the sample processing system viewed from above.

The sample processing system 1 of the present embodiment includes a receiving unit 21, tube sorter 22, relay unit 23, relay unit 24, recovery unit 25, transport units 31 through 33, blood cell analyzer 6, smear sample preparation apparatus 43, and transport controller 7. The blood cell analyzer 6 includes an information processing unit 5, and measuring units 41 and 42. The sample processing system 1 is connected to a host computer 8 via a communication network and is capable of communication.

The receiving unit 21, tube sorter 22, relay units 23 and 24, recovery unit 25, and transport units 31 through 33 are arranged adjacently left to right to be capable of delivering the sample rack L. A plurality of sample racks L capable of holding ten sample tubes T each are installed in these units and the apparatus. The sample rack L is transported in the arrow direction in FIG. 1. The tube sorter 22 has a transport path r1 for transporting the sample rack L in the leftward direction, and a transport path r2 for transporting the sample rack L in the rightward direction.

Figure 2A:
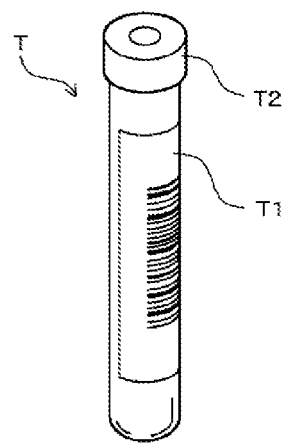
FIG. 2A shows a sample tube.
Figure 2B:
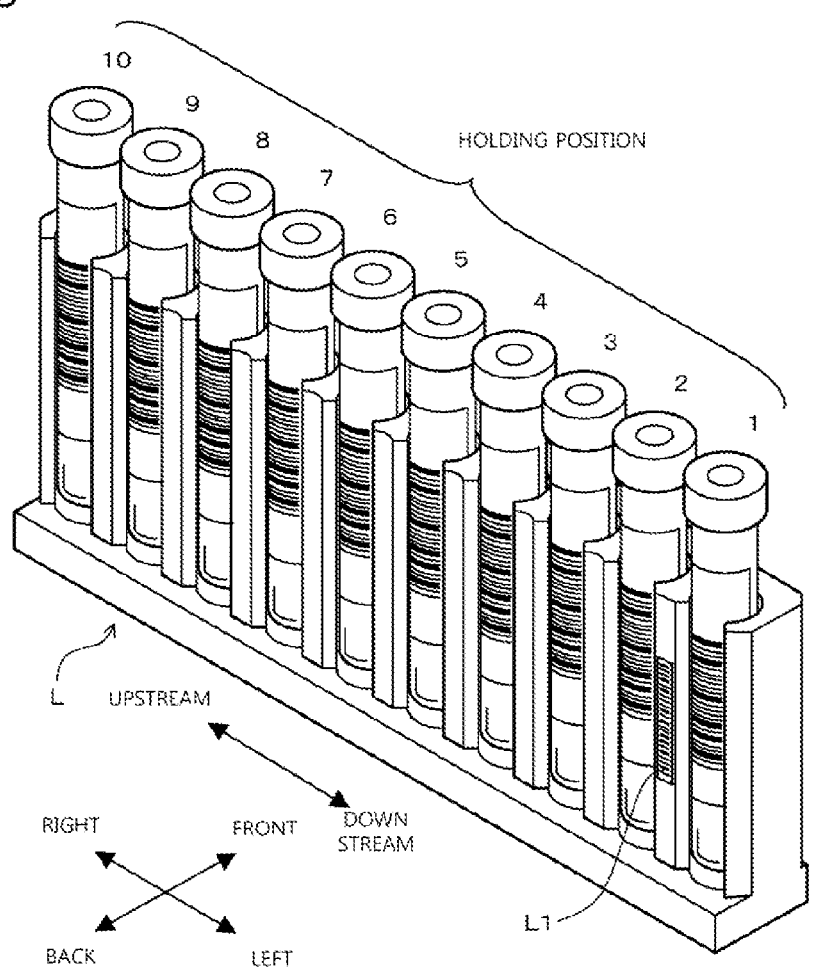
FIG. 2B shows a sample rack.

FIGS. 2A and 2B respectively show the structures of the sample tube T and the sample rack L. FIG. 2A is a perspective view showing the exterior of the sample tube T; FIG. 2B is a perspective view showing the exterior of the sample rack L holding ten sample tubes T. FIG. 2B also shows the direction (front to back and left to right directions in FIG. 1 of the sample rack during transport.

Referring to FIG. 2A, the sample tube T is a tube-like container, open at the top end, and formed of transparent synthetic resin or glass. A barcode label T1 is adhered to the side surface of the sample tube T. A barcode which includes the sample ID is printed on the barcode label T1. The sample tube T contains a blood sample of whole blood collected from a patient, and the opening at the top end is sealed with a rubber cap T 2.

Referring to FIG. 2B, a barcode label L1 is adhered to the back side of the sample rack L. A barcode indicating the rack ID is printed on the barcode label L1. The sample rack L has holders capable of vertically holding ten sample tubes T. For convenience, the position of each holder is referred to by holding positions 1 through 10 arranged in ascending order from the downstream side to the upstream side in the transport direction.

Returning to FIG. 1, when the user starts a measurement of a sample, the sample tube T containing the sample is first set in the sample rack L, and the sample rack L is loaded in the receiving unit 21. The sample rack L loaded in the receiving unit 21 is transported backward to the tube sorter 22.

The tube sorter 22 includes a barcode unit 120 and storage section 100. The storage section 100 includes buffer rack 140, six archive racks R1, and one sorting rack R2. The buffer rack 140, six archive racks R1, and one sorting rack R2 respectively have a plurality of holders for holding the sample tubes T, as shall be described later. A space for the installation of the sample rack L is provided in front of the sorting rack R2, and five sample racks L can be accommodated in this space.

The tube sorter 22 first performs processing by the barcode unit 120 on the sample rack L delivered from the receiving unit 21 to the tube sorter 22. Specifically, the barcode unit 120 reads the rack ID from the barcode label L1 on the sample rack L1, detects the holding position at which the sample tube T is held in the sample rack L, and reads the sample ID from the barcode label T1 of the sample tube T. The tube sorter 22 transmits the sample ID read by the barcode unit 120 through the transport controller 7 to the host computer 8. The host computer 8 prepares, based on the measurement order and analysis result of each sample, information (hereinafter referred to as "transfer information") which will be referred by the tube sorter 22 for transferring the sample tube T. The tube sorter 22 also receives transfer information from the host computer 8 through the transport controller 7.

Then, the tuber sorter 22 transfers the sample tube T held in the sample rack L to one of the racks in the storage section 100, buffer rack 140, archive rack R1, sorting rack R2 or sample rack L loaded in front of the buffer rack 140, according to the received transfer information. The tube sorter 22 can transfer the sample tube T held in the buffer rack 140 to the sample rack L on the transport path r1. Thereafter, the sample rack L is delivered to the relay unit 23.

The sample rack L which has been delivered from the tube sorter 22 to the relay unit 23 is then delivered to the relay unit 24 when the destination of the sample rack L is in a leftward direction. On the other hand the sample rack which has been delivered from the tube sorter 22 to the relay unit 23 is then delivered in front of the relay unit 23 for delivery to the tube sorter 22 when the destination is in a rightward direction. The sample rack L which has been delivered from the relay unit 23 to the relay unit 24 is moved to the front of the relay unit 24, and thereafter delivered to the transporting unit 31.

The transporting units 31 through 33 are respectively configured to transport the sample rack L delivered from the upstream side in accordance with the instructions of the transport controller 7. Specifically, the transporting units 31 through 33 transports the received sample rack L in the backward direction, when a sample tube T held by the sample rack L delivered from the upstream side is to be processed by the corresponding module (i.e., the units 41, 42 or the apparatus 43), to a position in front of the corresponding unit or apparatus. When processing is not to be performed by the measuring units 41 and 42, the transporting units 31 and 32 move the sample rack L delivered from the upstream side straight ahead in the leftward direction, and sequentially deliver to the transporting unit on the downstream side.

The measuring units 41 and 42 are respectively configured to remove the sample tube T from the sample rack L delivered to the forward position, and to measure the sample contained in the sample tube T. The information processing unit 5 receives and analyzes the measurement data from the measuring units 41 and 42, and prepares analysis results that include each analysis value of the measurement items. The information processing unit 5 is connected beforehand to the host computer 8 and is capable of communication therewith, and transmits the analysis results to the host computer 8.

The smear sample preparation apparatus 43 is configured to aspirate the sample from the sample tube T held in the sample rack L at the forward position, and to prepare a smear sample from the aspirated sample. The smear sample preparation apparatus 43 is connected to the host computer 8 and is capable of communication therewith. The smear sample preparation apparatus 43 transmits a message indicating the smear sample preparation has been completed to the host computer 8.

When the processing by the measuring units 41 and 42 and the smear sample preparation apparatus 43 is completed and there is no need for processing on the downstream side, the sample rack L is transported forward into the transporting unit, and thereafter moved to the upstream side by the transporting unit. Thus, the sample rack L is moved to the upstream side.

The sample rack L which is transported from the transporting units 31 through 33 to the upstream side is moved in the rightward direction by the relay unit 24 and relay unit 23, and delivered to the tube sorter 22. The tube sorter 22 moves the sample rack L received from the relay unit 23 to the receiving unit 21.

The sample rack L delivered from the tube sorter 22 to the receiving unit 21 is moved to the back in the receiving unit 21 to be again delivered to the tube sorter 22. In this case, the barcode unit 120 performs the reading process similar to above. The tube sorter 22 receives the transfer information from the host computer 8 and transfers the sample tube T held in the sample rack L in accordance with the received transfer information.

A sample tube T which does not require re-examination by the measuring units 41 and 42 or smear sample preparation (hereinafter referred to simply as "re-examination") by the smear sample preparation apparatus 43, and a sample tube T which does not require processing outside the sample processing system 1 is transferred to the archive rack R1. A sample tube T which does not require the re-examination but does require processing outside the sample processing system 1 is transferred to the sorting rack R2. A sample tube T which requires the re-examination is transferred to a suitable sample rack L as already explained, then delivered to the relay unit 23. Processing of a sample tube T by the sample processing system 1 is completed by transferring the sample tube T to the archive rack R1 or the sorting rack R2.

When all the held sample tubes T have been transferred and the empty sample rack L is delivered to the relay unit 23, the sample rack L is moved forward by the relay unit 23 and thereafter again delivered to the tube sorter 22. The tube sorter 22 moves the empty sample rack L received from the relay unit 23 to the receiving unit 21. The empty sample rack L delivered to the receiving unit 21 is transported in a rightward direction by the receiving unit 21 and delivered to the recovery unit 25. The sample rack L is then moved to the back of the recovery unit 25 and stored in the recovery unit 25. The transport of the sample rack L is thus completed.

The transport controller 7 is connected to the receiving unit 21, tube sorter 22, relay units 23 and 24, recovery unit 25, and transporting units 31 through 33 and is capable of communication therewith so as to control the transport operations of the sample rack L via these units. The host computer 8 associates the sample ID and stores the sample measurement order, and sample analysis results. The host computer 8 is memorized with rules for transferring sample tubes T within the tube sorter 22.

Figure 3:
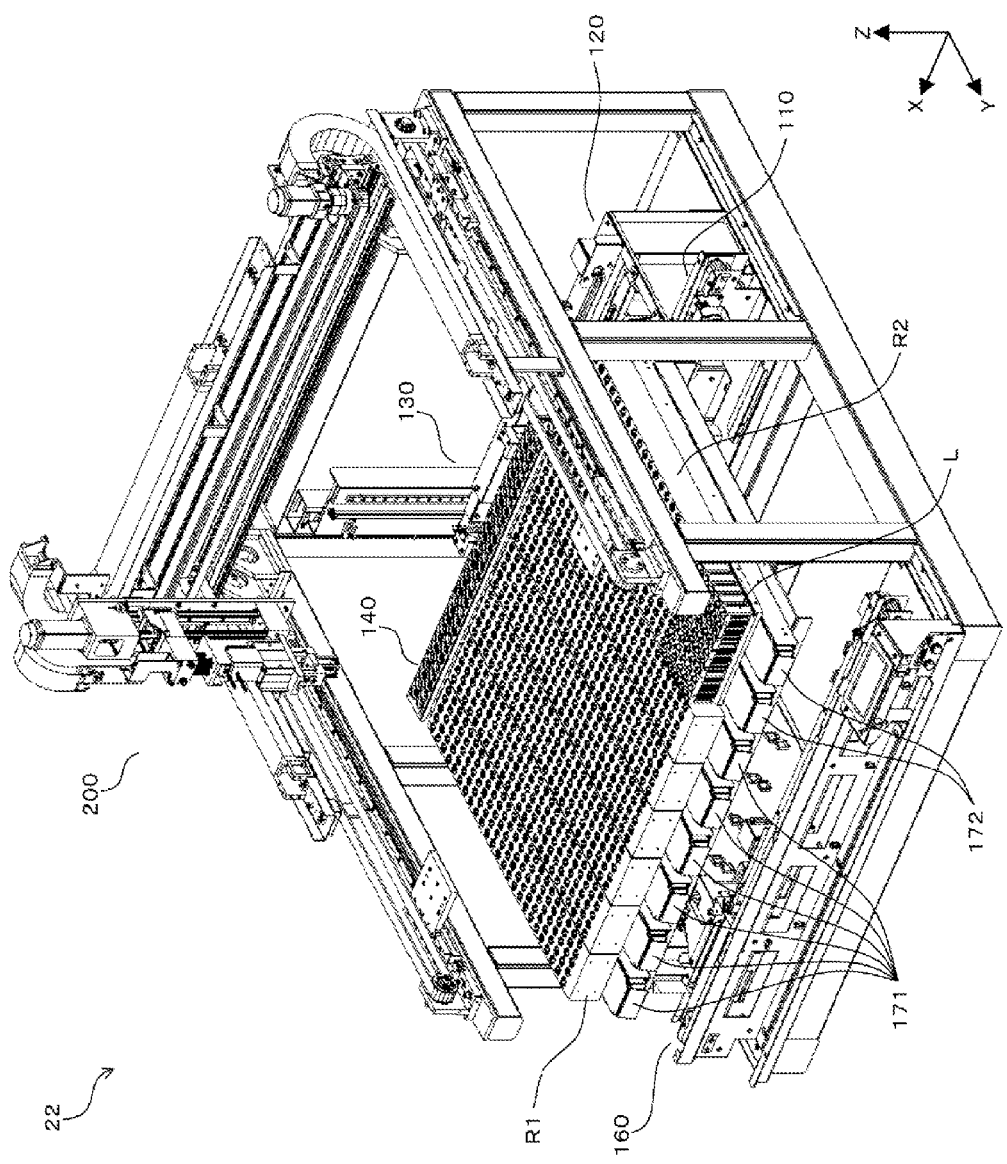
FIG. 3 is a perspective view showing the internal structure of the tube sorter.

FIG. 3 is a perspective view showing the internal structure of the tube sorter 22. The X-axis positive direction, Y-axis positive direction, and Z-axis positive direction shown in FIG. 3 correspond to the leftward direction, front direction, and upward direction, respectively.

In addition to the barcode unit 120 shown in FIG. 1, the tube sorter 22 also internally includes a tube transferring section 200, a transporting section 110, a lifting section 130, an empty rack storage 150 (refer to FIG. 4), a transporting section 160, six trays 171, and two trays 172.

The tube transferring section 200 moves the sample tube T inside the tube sorter 22. The transporting section 110 moves the sample rack L, which is delivered from the receiving unit 21, in a leftward direction along the transport path r1 (refer to FIG. 1). The lifting section 130 lifts up the sample rack L when the sample rack L is disposed at a predetermined position on the transport path r1 . The transporting section 160 moves the sample rack L, which is delivered from the relay unit 23, in a rightward direction along the transport path r2 (refer to FIG. 1).

Sixty holders 141 are formed on the buffer rack 140. One hundred twenty-five holders R11 are formed on one archive rack R1 . Two hundred holders R21 are formed on the sorting rack R2.

The tray 171 supports the archive rack R1 , and is movable in the forward direction from the state shown in FIG. 3. Two trays 172 support the sorting rack R2 and the sample racks L loaded in the forward part of the sorting rack R2, and are movable in the forward direction from the state shown in FIG. 3. The two trays 172 are also configured to move front to back in mutual connection. The storage 100 and the trays 171 and 172 supporting the storage 100 are at a higher level than the transport sections 110 and 160. More specifically, they are at a higher level than the top part (cap part T2 ) of the sample tube T being transported by the transporting sections 110 and 160. Hence, the respective six archive racks R1 can be moved across over the transporting section 160, and they can be drawn separately in the forward direction through an opening formed in the cover (not shown in the drawing) which covers the internal part of the tube sorter 22. The sorting rack R2 and the sample rack L loaded at the forward part of the sorting rack R2 can be drawn forward similar to the archive rack R1.

Figure 4:
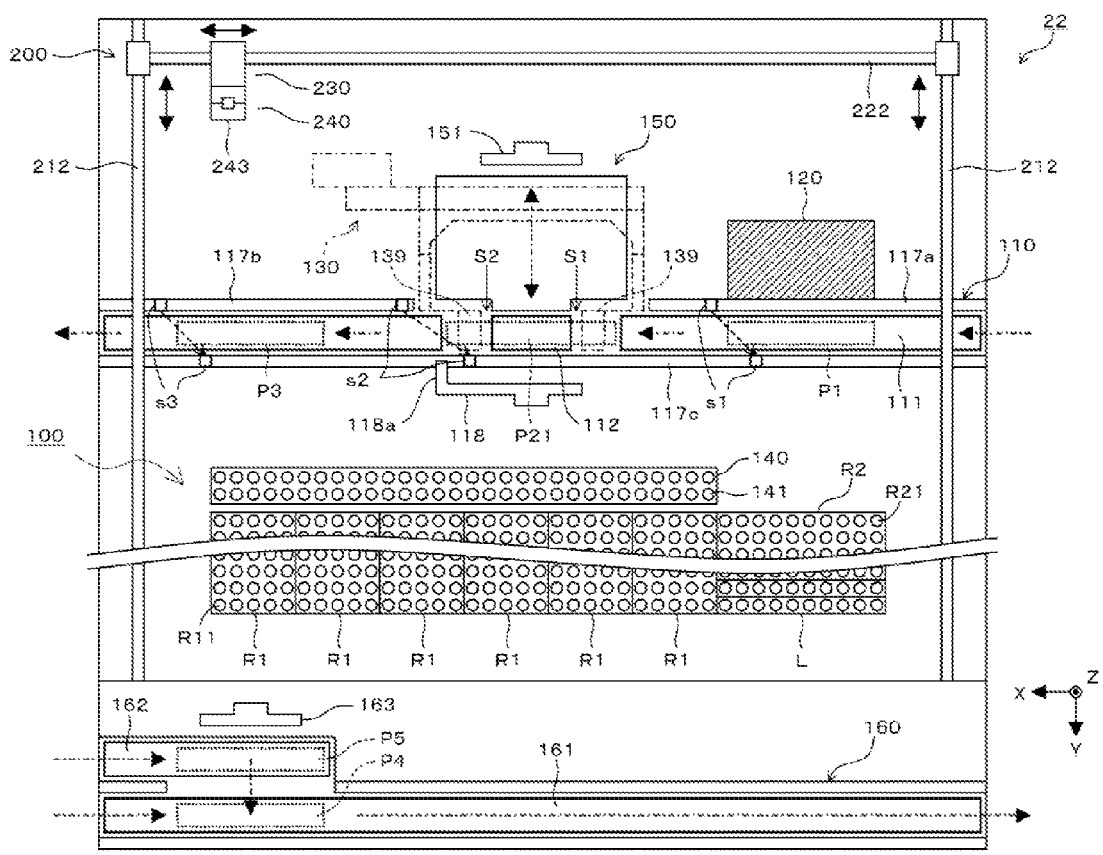
FIG. 4 is a schematic view of the internal part of the tube sorter viewed from above.

FIG. 4 is a schematic view of the internal part of the tube sorter 22 viewed from above. Note that the lifting section 130 is indicated by dashed lines for convenience in FIG. 4.

The tube transferring section 200 includes two rails 212 which extend in the front to back direction, rail 222 which extends in the left to right direction, supports 230 and 240. The rails 212 are fixedly attached inside the tube sorter 22, whereas the rail 222 is movable in the front to back direction along the rails 212. The supporting part 230 is movable in the left to right direction along the rail 222. The supporting part 240 is movable in the vertical direction along the supporting part 230. A gripper 243 for gripping the sample tube T is provided at the bottom end of the supporting part 240. The structure of the tube transferring section 200 is described later with reference to FIGS. 6A and 6B, and FIG. 7.

The transporting section 110 has belts 111 and 112 which extend in right to left directions, walls 117a through 117c provided at the front and back of the belts 111 and 112, and rack extracting device 118. The sample rack L loaded on the belts 111 and 112 is transported in the leftward direction by the movement of the belts 111 and 112 in the leftward direction.

Figure 5A:
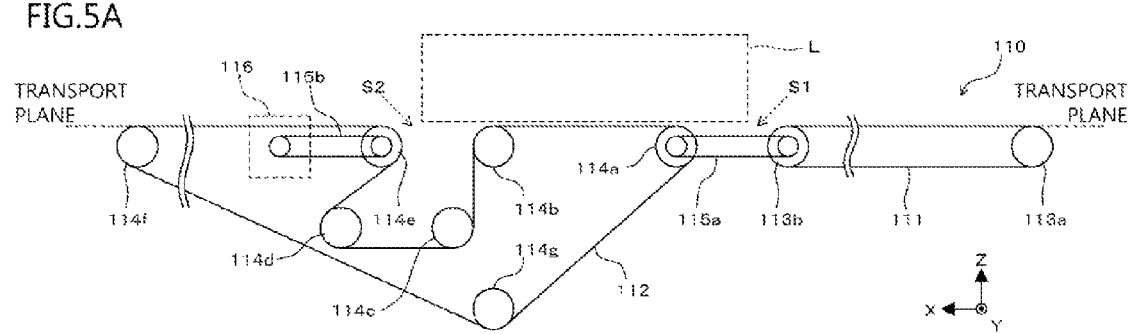
FIG. 5A is a schematic view showing the structure when viewing the transporting section from the front.

FIG. 5A is a schematic view showing the structure when viewing the transporting section 110 from the front (Y-axis negative direction).

In addition to the belts 111 and 112, the transporting section 110 also has pulleys 113a and 113b, 114a through 114g, belts 115a and 115b, and a motor 116. The belt 111 is looped around the pulleys 113a and 113b, and the belt 112 is looped around the pulleys 114a through 114g. The pulleys 113b and 114 has shafts projecting on the forward side (Y-axis positive direction) and the belt 115a is looped around the shafts of the pulleys 113b and 114a. The pulley 114e also has a shaft projecting on the forward side and the belt 115b is looped around the shaft of the pulley 114e and the shaft of the motor 116 on the front side of the belt 112. The motor 116 is positioned at the front side of the belt 115b.

When the motor 116 is actuated, the pulley 114e is rotated through the belt 115b, thus rotating the pulleys 114a through 114g. When the pulley 114a is rotated, the pulley 113b is rotated through the pulley 115a, thus rotating the pulley 113a. The belts 111 and 112 moved around the periphery of the pulleys in accordance with the rotation of the shaft of the motor 116.

A space S1 is formed between the pulleys 113b and 114a. A space S2 is formed between the pulleys 114b and 114e. The size of the spaces S1 and S2 are sufficient to allow the insertion of the supporting part 139 of the lifting section 130, as shown in FIG. 4. The top surface of the belt 111 between the pulleys 113a and 113b, the top surface of the belt 112 between the pulleys 114a and 114b, and the top surface of the belt 112 between the pulleys 114e and 114f are set at the same level. These surfaces are referred to as "transport plane" hereinafter. The top edge of the walls 117a through 117c (refer to FIG. 4) are positioned somewhat higher than the transport plane, and the width in the front to back direction of the walls 117a, 117b, and wall 117c is set so as to allow passage of one sample rack L.

Returning to FIG. 4, the sample rack L delivered from the receiving unit 21 is moved in the leftward direction by the belt 111, and disposed at the position P1 opposite the barcode unit 120. The sample rack L set at the position P1 is detected by a sensor s1. The barcode unit 120 detects the holding positions at which sample tubes T are held in the sample rack L, and reads the sample ID of each.

Figure 5B:
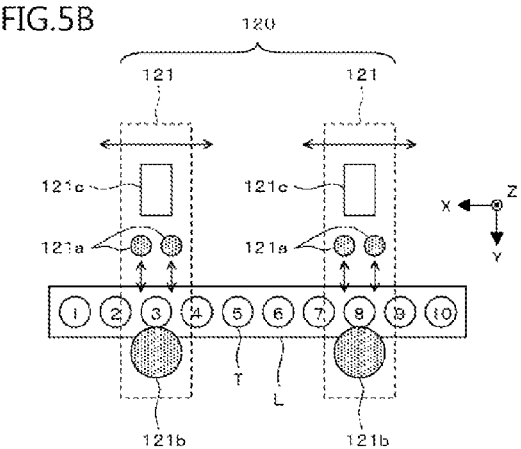
FIGS. 5B and 5C illustrate reading operation performed by the barcode unit.
Figure 5C:
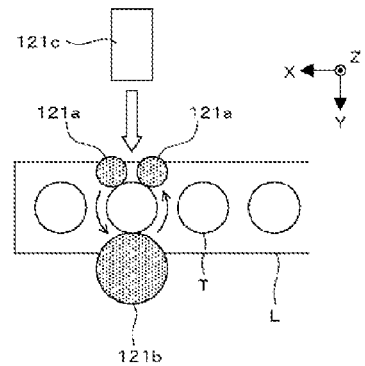

FIGS. 5B and 5C illustrate reading operation performed by the barcode unit 120.

Referring to FIG. 5B, the barcode unit 120 has two moving parts 121 arranged in right to left direction. The two moving parts 121 are movable in the right to left direction. The moving parts 121 each have two rollers 121a, a roller 121b, and barcode reader 121c. The barcode reader 121c is fixedly mounted on the moving part 121. The barcode reader 121c reads the rack ID from the barcode label L1 positioned at the front, and reads the sample ID from the barcode label T1.

The moving part 121 on the left side is sequentially disposed at positions corresponding to the holding positions 1 through 5. The moving part 121 on the right side is sequentially disposed at positions corresponding to the holding positions 6 through 10. As shown in FIG. 5C, the moving part 121 moves the two rollers 121a at each holding position. When the roller 121a are moved in the forward direction a distance to abut the sample tube T, the presence or absence of the sample tube T at the holding position is detected. When the roller 121a abuts the sample tube T, the roller 121b is rotated and the barcode label T1 is read.

Returning to FIG. 4, when the detection and reading operations by the barcode unit 120 are completed, the tube sorter 22 transmits the read sample ID to the host computer 8 and receives the transfer information from the host computer 8 as previously described. When the sample tube T requires transfer to the sample rack L according to the transfer information, the sample rack L is moved in the leftward direction by the belts 111 and 112. The sample rack L is moved until it abuts the flange 118a of the rack extracting device 118, and disposed at the position P21. The sample rack L set at the position P21 is detected by a sensor s2. When the sample tube T does not require transfer to the sample rack L according to the transfer information, the sample rack L is moved in the leftward direction by the belts 111 and 112 so as to pass through the position P21, and is disposed at the position P3. The sample rack L set at the position P3 is detected by a sensor s3. The sample rack L disposed at position P3 is then moved in the leftward direction and delivered to the relay unit 23.

The sample rack L disposed at position P21 is lifted up (Z-axis positive direction) by the lifting section 130 to the position P22 (refer to FIG. 9C). When the sample rack L is positioned at the position P22, the sample tube T requires to be transferred is removed from the sample rack L and moved to the destination rack of the storage 100. If a sample tubes T to be transferred to the sample rack L is held in the buffer rack 140, it is then removed from the buffer rack 140 and set in the sample rack L. When the transfer of the sample tube T to/from the sample rack L is completed, the sample rack L is lowered by the lifting section 130 and again disposed at the position P21. The sample rack L is then moved in the leftward direction by the belt 112 to the position P3. The sample rack L disposed at position P3 is delivered to the relay unit 23.

If all sample tubes T have been removed from the sample rack L at position P22 and the sample rack L has become empty, it is moved from the position P21 to the empty rack storage 150 by the rack extracting device 118 pushing the rack surface on the front side. When the number of sample tubes T held in the buffer rack 140 reaches a predetermined value, the empty sample rack L stored in the empty rack storage 150 is pushed from the storage 150 to the position P21 by the rack extracting device 151. And it is lifted and disposed at the position P22 by the lifting section 130. The sample tubes T in the buffer rack 140 are then transferred to the sample rack L.

The sample rack L moved from the relay unit 23 to the transporting section 160 is transported in the rightward direction by the belt 161 or the belt 162 of the transporting section 160, and disposed at position P4 or position P5. The sample rack L disposed at position P5 is then moved to position P4 by the rack extracting device 163 pushing on the surface on the back side. The sample rack L disposed at position P4 is then moved in the rightward direction by the belt 161 and delivered to the receiving unit 21.

Figure 6A:
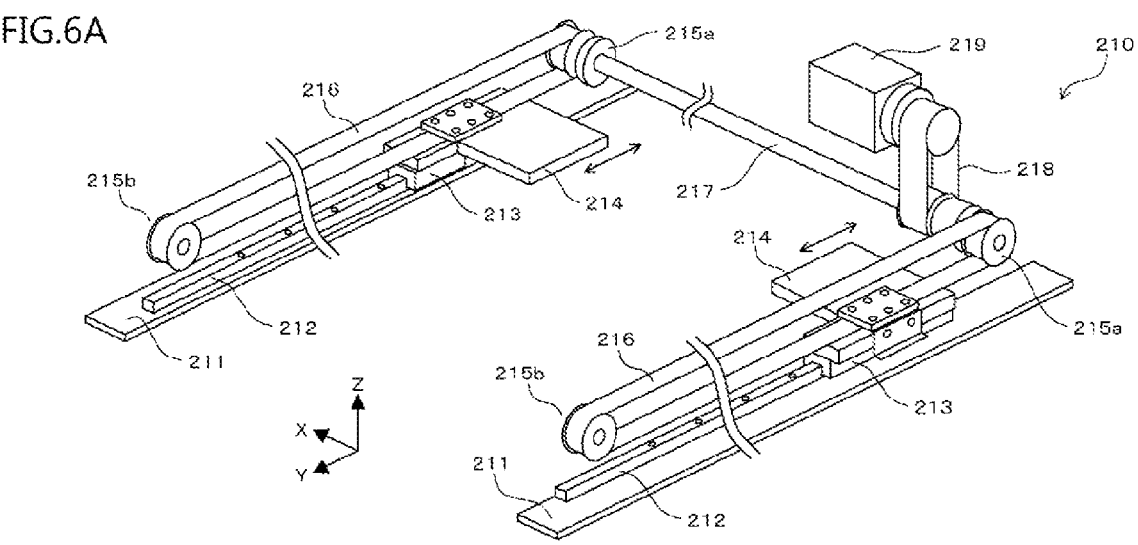
FIGS. 6A and 6B are schematic views of the structure of the supporting part of the tube transferring unit.

FIG. 6A is a schematic view of the structure of the supporting structure 210 of the tube transferring section 200.

A pair of support plates 211 which extend in the front to back direction are arranged at the left end and right end of the tube sorter 22. The rails 212 are disposed on the support plate 211. A sliding part 213 is slidable in the Y-axis direction relative to the rail 212. A support member 214 is fixedly mounted on the sliding part 213. Pulleys 215a and 215b are installed at the front end and near the back end of the rail 212. Belts 216 are respectively looped around the pairs of pulleys 215a and 215b. The support member 214 is fixedly mounted on the belt 216. The right side pulley 215a and the left side pulley 215a are connected with the shaft 217. The shaft of a motor 219 is connected to the shaft 217 through a belt 218. The support members 214 on both sides can move along the Y-axis in mutual linkage via the drive force of the motor 219.

Figure 6B:
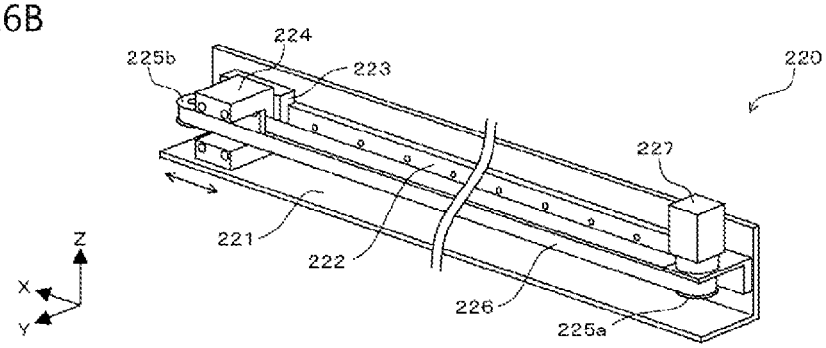

FIG. 6B is a schematic view of the structure of the supporting part 220 of the tube transferring section 200.

A support plate 221 extending in the X-axis direction is fixedly mounted on the pair of support members 214 of the supporting structure 210 (see FIG. 6A). The rail 222 is disposed on the support plate 221. A sliding part 223 is slidable in the X-axis direction relative to the rail 222. A support member 224 is fixedly mounted on the sliding part 223. The pulleys 225a and 225b are fixed on the support plate 221 near the left end and right end of the rail 222. The belt 226 is looped around pulleys 225a and 225b, and the support member 224 is attached to the belt 226. The shaft of the motor 227 is connected to the right side pulley 225a. The support member 224 can move along the X-axis via the drive force of the motor 227.

Figure 7:
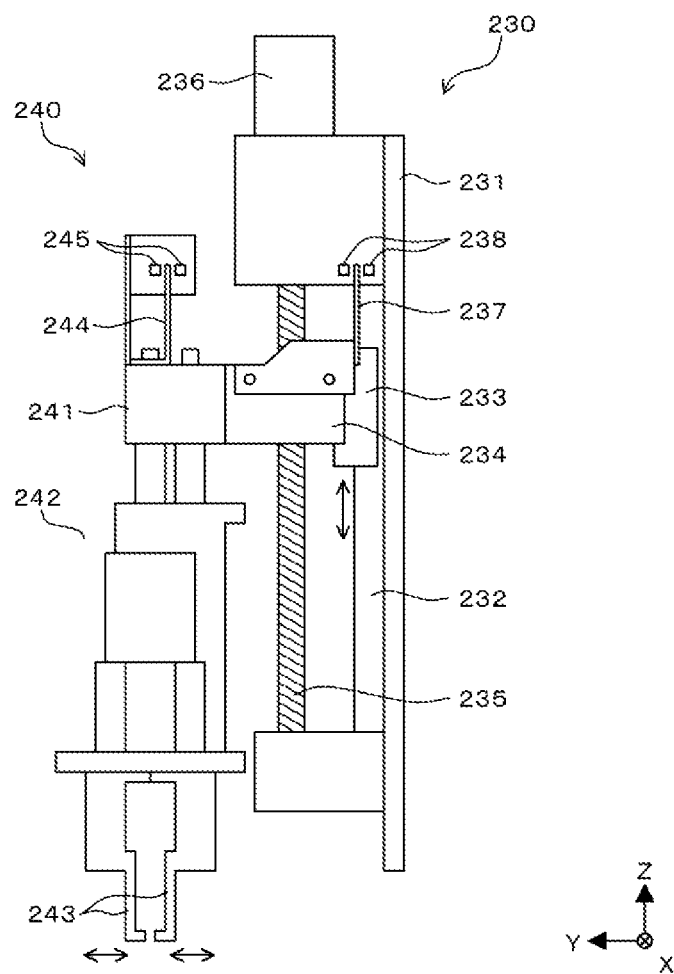
FIG. 7 is a schematic view of the structure of the supporting part of the tube transferring unit.

FIG. 7 is a schematic view of the structure of the supporting parts 230 and 240 of the tube transferring section 200.

The supporting part 230 is described below. The support plates 231 extending in the Z-axis direction are fixedly mounted on the support member 224 of the supporting part 220 (see FIG. 6B). The rail 232 is disposed on the support plate 231. A sliding part 233 is slidable in the Z-axis direction relative to the rail 232. A support member 234 is fixedly mounted on the sliding part 233. A shaft 235 extends in the Z-axis direction, and a screw type channel is formed in the shaft 235. The support member 234 is attached to the shaft 235 so as to be movable in the Z-axis direction along the channel of the shaft 235 when the shaft 235 is rotated around the Z-axis. The shaft of a motor 236 is connected to the top end of the shaft 235. When the motor 236 is actuated, the support member 234 moves along the Z-axis via the drive force of the motor 236.

A light shield 237 is installed on the support member 234, and a pair of sensors 238 for detecting intervening object are mounted on a member fixed on the support plate 231. When the support member 234 moves upward (Z-axis positive direction), the light shield 237 intervenes between the pair of sensors 238. Hence, the support member 234 is detectable at the uppermost side position.

The supporting part 240 is described below. The support member 241 is fixedly attached to the support member 234 of the supporting part 230. A support member 242 is mounted below the support member 241 via elastic material such as a spring. The gripper 243 capable of holding from the Y-axis direction the top part of a sample tube T is provided below the support member 242. The gripper 243 includes pieces movable to be approached or separated with each other. The gripper 243 grips the top part of a sample tube T by approaching the pieces and releases the gripped sample tube T by separating the pieces. According to this configuration, the gripper 243 is movable in front and back along the Y-axis by the supporting structure 210, movable in left and right along the X-axis by the supporting part 220, and movable in up and down along the Z-axis by the supporting part 230. Although the gripper 243 is configured to grip the sample tube T by pinching the tube with two pieces in the present embodiment, other configuration to grip a tube can be employed. For example, the gripper may be configured to catch the tube by applying a negative pressure to the top of tube.

A light shield 244 is provided at the top part of a member connecting the support members 241 and 242. When the gripper 243 is lowered and a force in the Z-axis positive direction is exerted by the gripper 243, the light shield 244 intervenes between the pair of sensors 245. Hence, the abutting of the gripper 243 against the cap T2 of the sample tube T is detected during lowering.

Figure 8:
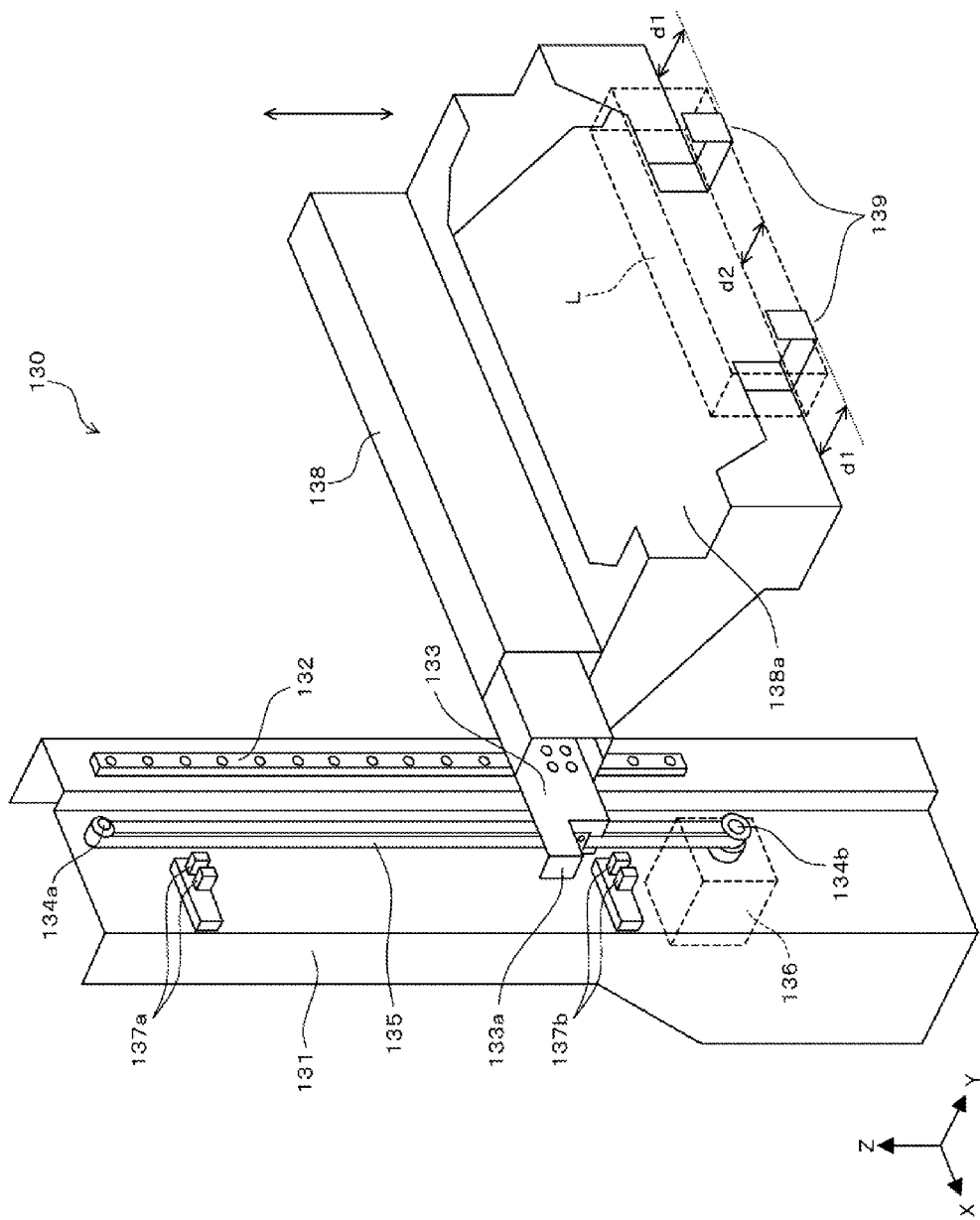
FIG. 8 is a schematic view showing the structure of the lifting section.

FIG. 8 is a schematic view showing the structure of the lifting section 130.

The lifting section 130 includes a support member 131 mounted inside the tube sorter 22, a rail 132 extending in the vertical direction and mounted on the support member 131, sliding part 133 which is slidable in the vertical direction relative to the rail 132, pulleys 134a and 134b mounted on the top part and bottom part of the support member 131, a belt 135 looped around the pulleys 134a and 134b, a motor 136 mounted behind the support member 131, a pair of light shield sensors 137a and 137b, a support body 138 mounted on the sliding part 133, and a pair of supporting parts 139 mounted on the front of the support body 138.

The shaft of the motor 136 is connected to the pulley 134b. When the motor 136 is actuated, the pulley 134b is rotated, thus rotating the belt 135. The support member 133 is fixedly mounted on the belt 135. The sliding part 133 moves along the rail 132 in the vertical direction via the movement of the belt 135. A flange 133a is formed on the left end of the sliding part 133. When the motor 136 is actuated, the flange 133a moves between the pair of sensors 137a and 137b. Hence, the sliding part 133, support body 138, and supporting part 139 are detected when positioned at the top end and the bottom end.

Each of the supporting part 139 has two walls arranged in front and back. The walls are separated by a width d1. The supporting part 139 is configured so that the width d1 in the Y-axis direction becomes greater than the width d2 in the lateral direction of the sample rack L. As shown in FIG. 8, when the support body 138 is driven in the upward direction while the horizontal surface of the supporting part 139 supports the bottom surface of the sample rack L, the sample rack L is moved upward. Formed in the support body 138 is an opening 138a, which is larger than the width of the sample rack L in the longitudinal direction and larger than the width in the height direction of the sample rack L holding the sample tubes T. The empty sample rack L set at the position P21 can be pushed to the empty rack storage 150 by the rack extracting device 118 through the opening 138a.

FIGS. 9A through 9C show sequence of transfer of the sample tube T.

As shown in FIG. 9A, the supporting part 139 is inserted beforehand into the spaces S1 and S2 shown in FIG. 4 and the horizontal surface of the supporting part 139 is positioned a predetermined distance below the transport plane. The state in which the supporting part 139 is positioned as shown in FIG. 9A is referred to below as the "standby state". Therefore, when the supporting part 139 is in the standby state, the sample rack L which has been transported in the X-axis positive direction from the position P1 is disposed at the position P21 as shown in FIG. 9B, or passes through the position P21 to the position P3.

When the sample rack L is disposed at the position P21 and the sample tube T held in the sample rack L is to be transferred, the supporting part 139 is moved upward and the sample rack L is lifted to the position P22 as shown in FIG. 9C. The state in which the supporting part 139 is positioned as shown in FIG. 9C is referred to below as the "lift state". Level of bottoms of holding positions of the sample rack L at position P22 is designated height H1.

The archive rack R1 and the buffer rack 140 are arranged at a predetermined height so that the height H2 of bottom of the holder R11 of the archive rack R1 and the height H3 of bottom of the supporting part 141 of the buffer rack 140 are equal to the height H1. Therefore, the heights H1, H2, and H3 are mutually equal when the sample rack L is disposed at the position P22. The sorting rack R2 and the sample rack L in front of the sorting rack R2 are also arranged at a predetermined height so that the height of the bottom of the supporting part R21 of the sorting rack R2 and the height of the bottoms of holding positions of the sample rack L set in front of the sorting rack L are equal to the height H1. That is, the heights of bottoms of holding positions of the storage 100 all are H1 in the present embodiment.

With the supporting part 139 in the lift state (sample rack L disposed at position P22), the sample tube T held in the sample rack L is transferred to the storage 100, and the sample tube T held in the buffer rack 140 is transferred to the sample rack L. When the transfer of the sample tube T to/from the sample rack L is completed, the supporting part 139 is lowered and returned to the state shown in FIG. 9B, and the sample rack L is transported in the X-axis positive direction by the belt 112. When an empty sample rack L is to be pushed from position P21 to the empty rack storage 150, the supporting part 139 is disposed below the state shown in FIG. 9A not to interfere the movement to the empty rack storage 150. The empty sample rack L is pushed in the Y-axis negative direction through the opening 138a of the support body 138.

When the sample tubes T are transferred to the archive rack R1, the sample tubes T are set sequentially from the leftmost archive rack R1. When a single archive rack R1 is full, the sample tubes T are set in the next adjacent archive rack R1. When the rightmost archive rack R1 is filled, the sample tubes T are transferred to the leftmost archive rack R1. Holders R11 are filled in order from the leftmost one of the front row (first row) of each archive rack R1. When the first row becomes full, sequentially one row back will be filled as shown in FIG. 9D.

Transferring the sample tubes T to the buffer rack 140, sorting rack R2, and sample rack L installed in front of the sorting rack R2 are performed similarly. The holders are filled with the transferred sample tubes T in order from the leftmost one of the first row within a predefined range, as shown in FIG. 9D.

FIGS. 10A through 10C illustrate the moving distance of the sample tube T when the transfer is performed.

FIG. 10A shows a comparative example in which the sample tube T is removed from the sample rack L disposed at the position P21. In this case, the sample tube T is first lifted up a distance a to the same height as the sample tube T held in the buffer rack 140 and the like. The sample tube T is then lifted up a distance Z1 so as to not contact the sample tube T held in the buffer rack 140. After moving in the X-axis direction and the Y-axis direction (XY direction), the sample tube T is lowered down a distance Z1 and set in the target holder R11, 141. In this case, the sample tube T travels distances $\alpha+Z1+Z1$ from removing to setting.

FIG. 10B shows a comparative example in which the sample rack L is lifted up to the position at a higher level than the position P22, then the sample rack L is moved by hypothetical device 180 in the Y-axis direction until near the target holder R11, 214. In this case, the device 180 moves the sample rack L in the Y-axis direction to near the target holder, then the sample tube T is lifted up, for example, a distance Z1 to remove the sample tube T from the sample rack L. After moving in the XY direction, the sample tube T is lowered down a distance $Z1+\beta$ and set in the target holder. In this case, the sample tube T travels distances $Z1+Z1+\beta$ from removing to setting.

FIG. 10C shows the transfer of the sample tube T to/from the sample rack L of the present embodiment. In this case, the sample tube T is first lifted up a distance Z1 to remove the sample tube T from the sample rack L. After moving in the XY direction, the sample tube T is lowered down a distance Z1 and set in the target holder. In this case, the sample tube T travels distances Z1+Z1 from removing to setting. The moving distance in the XY direction this time is identical to that shown in FIG. 10A, and greater than that shown in FIG. 10B.

The moving distance of the sample tube T in the vertical direction in the present embodiment is decreased by the distance $\alpha$ from the comparative example of FIG. 10A. In the present embodiment, the transfer of the sample tube T to/from the sample rack L can be performed rapidly compared to the comparative example shown in FIG. 10A.

In comparison with the comparative example of FIG. 10B, although the moving distance in the vertical direction is decreased by distance $\beta$ in the present embodiment, the moving distance in the XY direction in the present embodiment is greater than the comparative example of FIG. 10B. In the case of the comparative example of FIG. 10B, however, a device 180 is required to move the sample rack L in the XY direction. A comparative example of FIG. 10B also complicates the structure of the tube sorter 22 since the examples requires a mechanism to transfer the sample rack L at the position P22 to the device 180. Moreover, in the comparative example of FIG. 10B, the sample rack L will be frequently swung when moved by the device 180, and the sample rack L is unstable. When the sample rack L is unstable, there may be a collision when the gripper 243 grasps the sample tube T. It may cause a failure of grip. To avoid this, there must be a waiting time after the XY movement by the device 180, which impairs higher speed processing. In the comparative example of FIG. 10B, the moving distance $\Delta L$ in the Y-axis direction of the sample tube T should be reduced as short as possible to rapidly transfer the sample tube T. If the moving distance $\Delta L$ is reduced, since the position of the device 180 and the position of the target holder are quite near in the Y-axis direction, the device 180 may obstruct the travel of the sample tube T from the sample rack L to the target holder. To avoid this, the device 180 must be frequently moved away from the target holder in the Y-axis direction after the sample tube T is removed from the sample rack L. This procedure further destabilizes the sample rack L. On the other hand, in the present embodiment the structure of the tube sorter 22 is simplified compared to the comparative example of FIG. 10B because the transfer of the sample tube T is performed while the sample rack L is stopped at position P22. In addition, the sample tube T is held stably in the sample rack L during the transfer of the sample tube T. Thus, the present embodiment provides rapid and stable transfer of the sample tube T to the supporting part via a simple structure.

In the present embodiment, a blood collection tube is used as the sample tube T. In this case, the distance Z1 may be set at a length the same as or longer than the entire length of the longest blood collection tube among blood collection tubes expected to the used in the sample processing system 1. The transferred blood collection tube can therefore be transported without colliding with the blood collection tube held in the archive rack R1. Z1 is preferably a total of entire length of the longest blood collection tube and a margin. Z1 is, for example, 1 mm to 20 mm, and more preferably 5 mm to 10 mm longer than the entire length of the tube. For example, when the longest blood collection tube is 125 mm in length, Z1 is preferably set within a range of 126 to 145 mm, and more preferably within a range of 130 to 135 mm.

Figure 11:
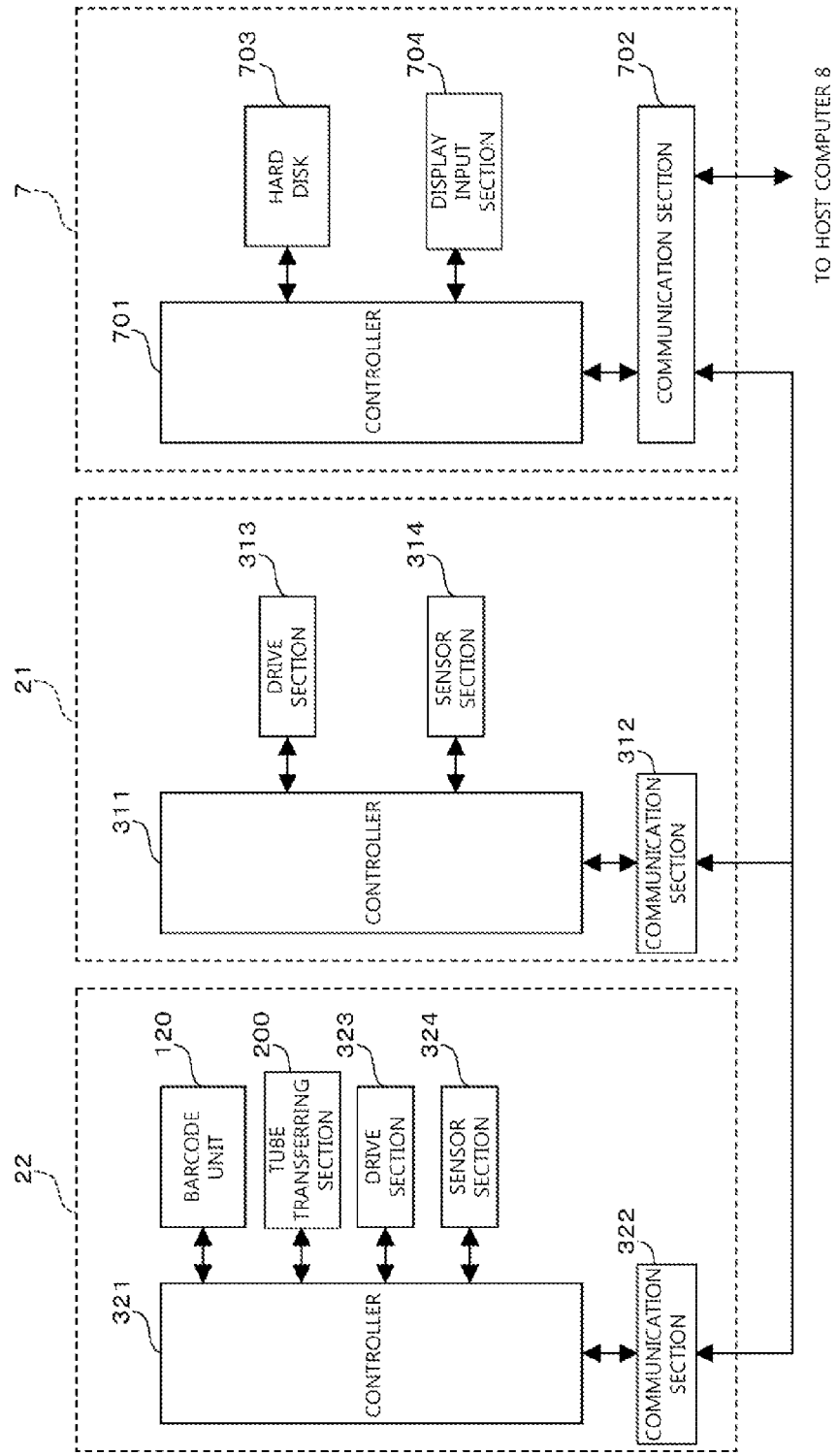
FIG. 11 shows the structures of the tube sorter, receiving unit, and transport controller.

FIG. 11 shows the structure of the tube sorter 22, receiving unit 21, and transport controller 7.

The tube sorter 22 includes a controller 321, communication section 322, barcode unit 120, tube transferring section 200, drive section 323, and sensor section 324. The controller 321 controls each section in the tube sorter 22, and receives signals output from each section in the tube sorter 22. The controller 321 also communicates with the transport controller 7 through the communication section 322.

The drive section 323 includes motors 116, 219, 227, 236, and 136, a drive source for driving rack extracting devices 118, 151, and 163, and a drive source for driving the gripper 243. The sensor section 324 includes sensors s1 through s3, sensors 238, 245, 137a, and 137b.

In the present embodiment, each motor included in the drive section 323 is a servo motor. These motors can be precisely controlled without optical sensors to detect the positions of the members driven by the motors included in the drive section 323. Note that optical sensors (for example, sensors 137a and 137b of FIG. 8) also may be used to detect the positions of the members driven by the motors included in the drive section 323. Hence, each motor can be controlled with greater precision.

The receiving unit 21 includes a controller 311, communication section 312, drive section 313, and sensor section 314. The controller 311 controls each section in the receiving unit 21, and receives signals output from each section in the receiving unit 21. The controller 311 also communicates with the transport controller 7 through the communication section 312. Note that the relay units 23 and 24, and recovery unit 25 are configured identically as the receiving unit 21.

The transport controller 7 includes a controller 701, communication section 702, hard disk 703, and display/input section 704. The control section 701 communicates with the receiving unit 21, tube sorter 22, relay units 23 and 24, recovery unit 25, transporting units 31 through 33, and host computer 8 through the communication section 702.

Figure 12:
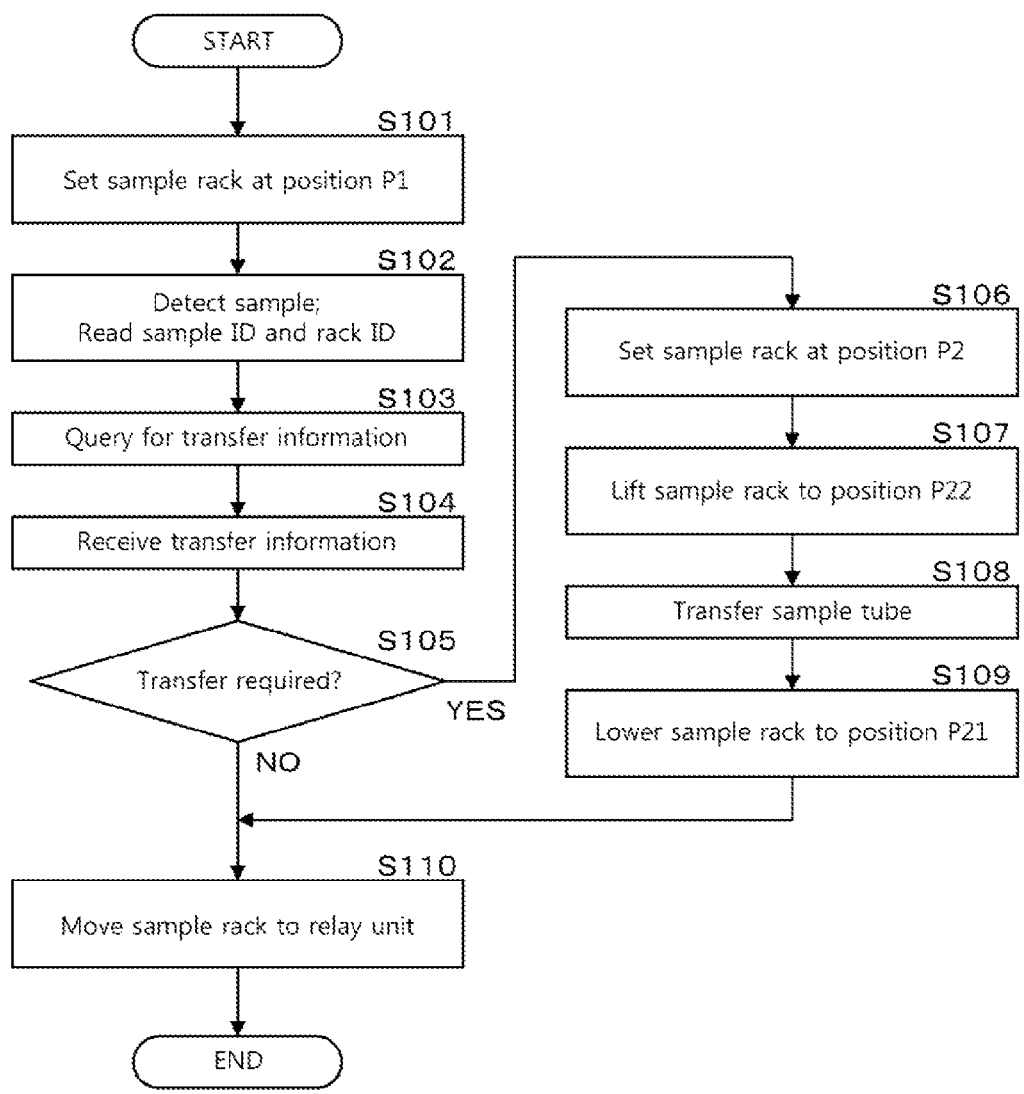
FIG. 12 is a flow chart showing the processing performed by the tube sorter.

FIG. 12 is a flow chart showing the processing performed by the tube sorter 22. The controller 321 is programmed to perform the steps in the flow chart. This processing starts when a sample rack L is delivered from the receiving unit 21 to the tube sorter 22.

The controller 321 of the tube sorter 22 controls the transport section 110 to transport the sample rack L delivered from the receiving unit 21 in a leftward direction via the belt 111, and to dispose the rack at position P1 (S101). The controller 321 then detects whether a sample tube T is held at a holding position on the sample rack L, and reads the sample ID and the rack ID via the barcode unit 120 (S102). The controller 321 then queries the host computer 8 for transfer information for the held sample tubes T (S103). Thereafter, the controller 321 receives the transfer information for all sample tubes T queried in S103 (S104).

Next, the controller 321 determines whether any sample tube T must be transferred to/from the sample rack L based on the transfer information received in S104 (S105). When no sample tube T requires transfer (S105: NO), the controller 321 controls the transport section 110 to transport the sample rack L disposed at the position P1 in the leftward direction via the belts 111 and 112, to pass the position P21 and to deliver the rack to the relay unit 23 (S110). Note that the sample rack L waits at position P1 when the supporting part 139 is not in the standby state or lift state, and the sample rack L passes through the position P21 when the supporting part 139 was in the standby state or lift state.

When there is a sample tube T requiring transfer (S105: YES), the controller 321 controls the transport section 110 to transport the sample rack L disposed at position P1 leftward via the belts 111 and 112, to the position P21 (S106). The controller 321 then controls the lifting section 130 to lift up the sample rack L disposed at the position P21, and places the rack at position P22 (S107). The controller 321 then controls the tube transfer section 200 to transfer the sample tube T requiring transfer to/from the sample rack L (S108).

When transfer is completed, the controller 321 controls the lifting section 130 to lower the sample rack L from the position P22 to the position P21 (S109). The controller 321 then controls the transport section 110 to transport the sample rack L at the position P21 in the leftward direction via the belts 111 and 112 to deliver the rack to the relay unit 23 (S110). Thus, the processing of the sample rack L delivered from the receiving unit 21 to the tube sorter 22 is completed.

The tube sorter 22 includes structures for precisely positioning the sample rack L at position P22 and for regulating a position shift of the sample rack L during transfer. The structure will be described below.

Figure 13A:
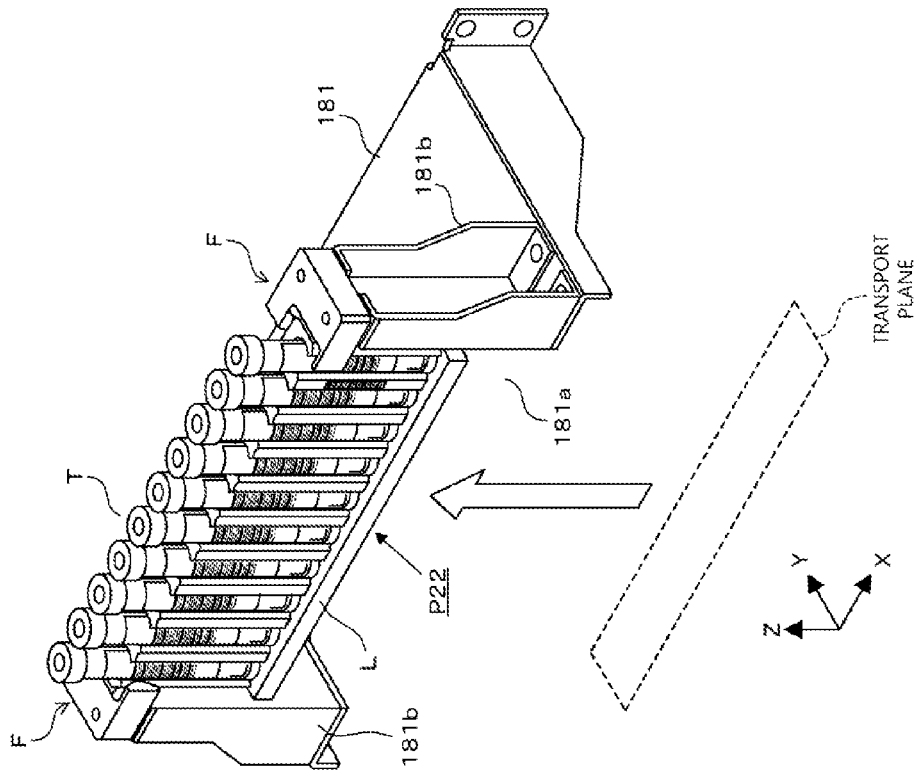
FIGS. 13A and 13B show the structure of the rack regulating member arranged inside the tube sorter.
Figure 13B:
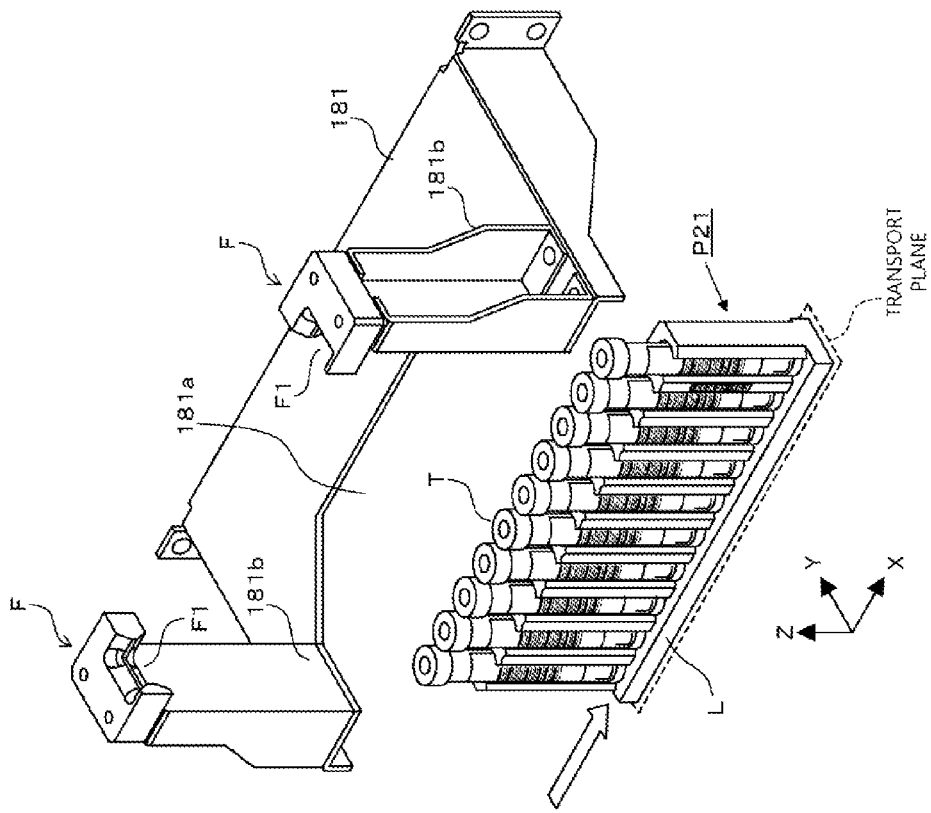

FIGS. 13A and 13B show the structures of the rack regulating members F and supporting part 181 arranged within the tube sorter 22. In FIGS. 13A and 13B, other devices (transport section 110, lifting section 130 and the like) are omitted for convenience.

The supporting part 181 is fixedly attached to the internal chassis (not shown in the drawing) of the tube sorter 22. A notch 181a is formed on the supporting part 181 in the Y-axis negative direction, and a member 181b is provided at positions circumscribing the notch 181a in the X-axis direction. Each of the rack regulating members F is fixedly attached to the top end of each member 181b. The rack regulating member F is provided above the position P21. A notch F1 is formed in the rack regulating member F. The thickness in the Y-axis positive side over the notch F1 is greater than the thickness in the Y-axis negative side. The two rack regulating members F are configured of a plastic resin and have mutually identical shapes. The rack regulating member F has a symmetrical shape, and can be mounted upside down to achieve similar function. In the state shown in FIGS. 13A and 13B, the two rack regulating members F are arranged to be mutually symmetrical in the YZ plane. The two rack regulating members F are also arranged so that the notches F1 mutually face each other.

When transferring the sample tube T as described above, the sample rack L is first disposed at the position P21 as shown in FIG. 13A. Then, the sample rack L at the position P21 is lifted up by the supporting part 139 of the lifting section 130 (refer to FIG. 8). The lifted sample rack L passes through the notch 181a and is disposed at region A (refer to FIG. 14B) defined by the notches F1 of the two rack regulating members F. The top surface of the sample rack L is then lifted up to a height substantially the same as the top surface of the rack regulating member F. The sample rack L is disposed at the position P22 as shown in FIG. 13B.

Figure 14B:
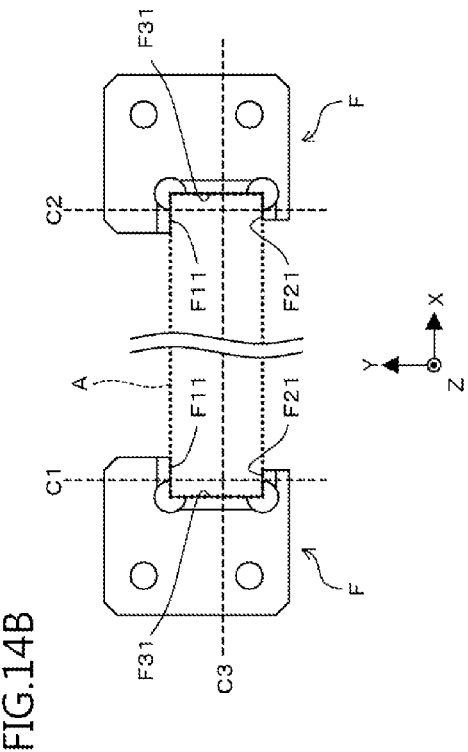
FIGS. 14B through 14D illustrate the positional relationship between the sample rack and the rack regulating member.
Figure 14D:
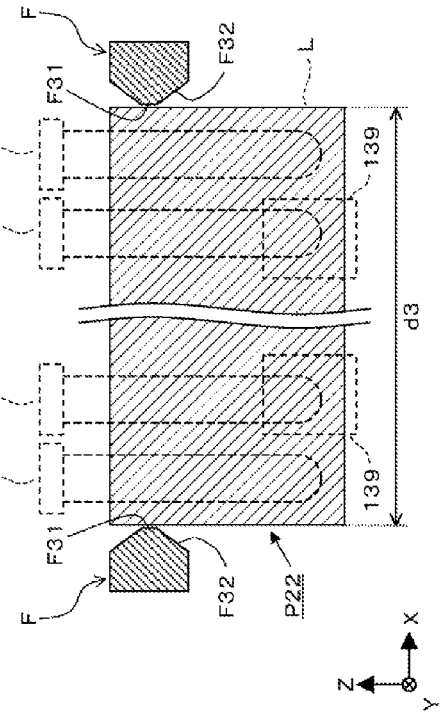
Figure 14A:
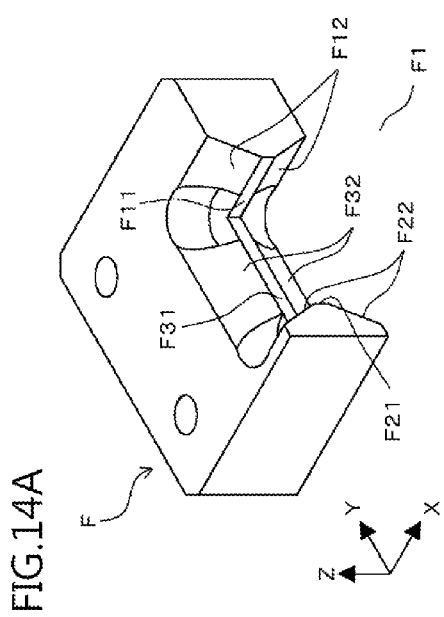
FIG. 14A shows the structure of the rack regulating member.

FIGS. 14A and 14B shows the detailed structure of the rack regulating member F. FIG. 14A shows the rack regulating member F on the left side in FIGS. 13A and 13B, and FIG. 14B is a planar view viewed from above of the two rack regulating members F of FIGS. 13A and 13B.

The notch F1 is defined by surfaces F11, F21, and F31, two inclined surfaces F12, two inclined surfaces F22, and two inclined surfaces F32. The surfaces F11 and F21 are parallel to the XZ plane, and surface F31 is parallel to the YZ plane. The inclined surfaces F12, F22, and F32 are formed at the top side and the bottom side of surfaces F11, F21, and F31, respectively. Concavities are formed in the inner side of the rack regulating member F between the inclined surfaces F12 and F32, and between the inclined surfaces F22 and F32. When the two rack regulating members F configured in this way are provided as shown in FIGS. 13A and 13B, the region A is defined in a plane parallel to the XY plane by the two openings F1 (specifically, the surfaces F11, F21, and F31).

Figure 14C:
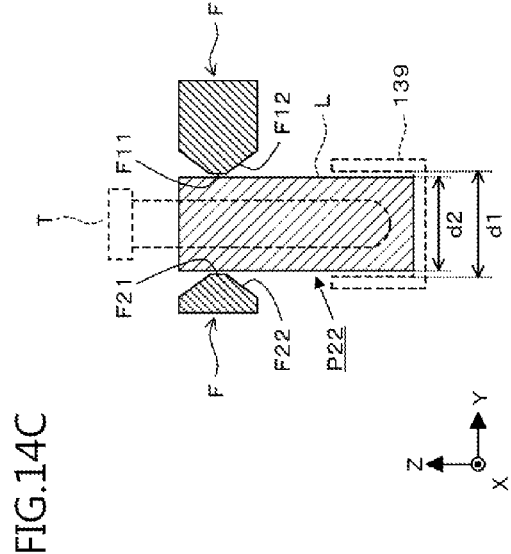

FIGS. 14C and 14D show the positional relationship between the rack regulating member F and the sample rack L disposed at position P22. FIG. 14C shows the cross section surfaces C1 and C2 parallel to the YZ plane (refer to FIG. 14B) viewed from the X-axis negative direction when the sample rack L is at position P22. FIG. 14D shows the cross section surface C3 parallel to the XZ plane (refer to FIG. 14B) viewed from the Y-axis positive direction when the sample rack L is at position P22. Note that in FIGS. 14C and D the positions of the sample tube T, sample rack L, and supporting part 139 are indicated by dashed lines.

Referring to FIG. 14C, the spacing of the surfaces F11 and F21 (width of region A in the Y-axis direction) is configured to be somewhat greater than the width d2 of the sample rack L in the lateral direction. The surfaces F11 and F21 are configured to be slightly separated from the side surface of the sample rack L disposed at position P22. The spacing of the inclined surfaces F12 and F22 in the Y-axis direction are configured to be greater than the spacing of the surfaces F11 and F21 in accordance with the separation with the surfaces F11 and F21 in the downward direction.

Referring to FIG. 14D, the spacing of the two surfaces F31 (width of region A in the X-axis direction) is configured to be somewhat greater than the width d3 of the sample rack L in the longitudinal direction. The two surfaces F31 are configured to be slightly separated from the side surface of the sample rack L disposed at position P22. The spacing of the two inclined surfaces F32 in the X-axis direction are configured to be greater than the spacing of the two surfaces F31 in accordance with the separation with the surfaces F31 in the downward direction.

When the two rack regulating members F are configured as above and arranged in the tube sorter 22, the sample rack L is guided to the position P22 without positional dislocation even when the sample rack L shifts within the XY plane due to collision and oscillation of the sample rack L when moving upward from position P21. Specifically, the sample rack L is guided within the region A and ultimately to position P22 by the end of the top surface of the lifted rack L abutting the bottom side of inclined surfaces F12, F22, and F32.

As shown in FIGS. 14C and D, the gripper 243 of the tube transferring section 200 (refer to FIG. 7) can smoothly remove the sample tube T held in the sample rack L disposed at position P22, since the sample rack L and the sample tube T thereon are always disposed at an intentional position. Moreover, the gripper 243 can smoothly sets the sample tube T removed from the buffer rack 140 to holding position of the sample rack L. Since the movement of the sample rack L is restricted within region A by the rack regulating members F, positional dislocation of the sample rack L is suppressed even when the sample rack L is vibrated or impacted when the gripper 243 sets or grasps the sample tube T, and the setting and removal of the sample tube T is unaffected thereafter.

Note that position P22 of the sample rack L is a position which puts the vicinity of the top end of the sample rack L within region A when the supporting part 139 of the lifting section 130 is in the raised state. That is, position P22 of the sample rack 1 is a position at which the transfer of the sample tube T can be smoothly performed by the gripper 243 because the vicinity of the top end of the sample rack L is within region A when the sample rack L is lifted up by the supporting part 139.

According to the present embodiment, the sample tubes T can be rapidly transferred as described below. Under such configuration where the storage 100 is arranged at a higher level than the transporting section 130, as in the present embodiment, a difference occurs in the levels in the vertical direction between the sample rack L disposed at position P21 and the storage 100. Therefore, when the sample tube T is individually transferred from the sample rack L disposed at position P21 to the storage 100, a long time is required to transfer all of the sample tubes T on the sample rack L because of the increase in the moving distance in the vertical direction of the sample tube T being transferred. In contrast, in the present embodiment the sample rack L is lifted up to position P22 by the supporting part 139 before transferring the sample tube T by the tube transferring section 200. Hence, the sample tube T can be rapidly transferred due to the reduction of the moving distance in the vertical direction of the sample tube T being transferred.

According to the present embodiment, the bottoms of holding positions of the sample rack 1 disposed at position P22 and the bottoms of holders of the storage 100 are at the same height. Therefore, the sample transfer control and sample sorter construction can be simple because the stroke removing the sample tube from the sample rack and the stroke setting the removed sample tube in the sample tube storage are substantially similar.

According to the present embodiment, the storage and trays 171 and 172 are at a higher level than the transporting sections 110 and 160, and, more specifically, are at a higher level than the top part (cap part T2) of the sample tube T being transported by the transporting section 160. Each section of the storage therefore can be drawn to the front separately. Even when the sample tube T is transported by the transporting section 160, each section of the storage can be drawn separately to remove the sample tube T outside the apparatus.

According to the present embodiment, the transfer of the sample tube T is performed by the tube transferring section 200 to sequentially fill the holders from the holder on the front side nearest the removal opening, as shown in FIG. 9D. Hence, amount to draw out the trays 171, 172 to remove the sample tube T in the storage 100 can be saved.

According to the present embodiment, the lifted sample rack L is disposed at position P22 by the rack regulating members F, and the movement of the rack L at position P22 is regulated within the XY plane (horizontal plane). The gripper 243 smoothly removes the sample tube T held in the sample rack L, and sets the removed sample tube T to the sample rack L smoothly.

According to the present invention, the inclined surfaces F12, F22, and F32 guide the sample rack L to the position P22 even when the sample rack L transferred upward from position P22 shifts within the XY plane. That is, the sample rack L can be guided gradually into the region A when the rack L is lifted up. Therefore, the lifted sample rack 1 can be smoothly disposed at position P22.

According to the present embodiment, the rack regulating member F has surfaces F11, F21, and F31 facing the top side surface of the lifted sample rack L as shown in FIGS. 14C and D, and the movement of the sample rack L is regulated by the surfaces F11, F21, and F31 abutting the top side surface of the sample rack L. The movement of the sample rack L therefore can be regulated efficiently with a simple structure compared to when using members arranged to face the entire side surface of the sample rack L.

According to the present embodiment, the rack regulating member F supports the four corners of the top part of the sample rack L which is formed as a rectangle in planar view. The movement of the sample rack L therefore is reliably regulated.

According to the present embodiment, the rack regulating member F is configured of plastic resin. Therefore, the rack regulating member F absorbs any impact when the sample rack L contacts the rack regulating member F, thus avoiding damage to the sample rack L.

Although the present invention has been described above by way of an embodiment, the present invention is not limited to this embodiment.

Although blood is the measurement object of the measuring units 41 and 42 in the above embodiment, types of samples to be measured and analyzed is not limited to blood. For example, urine, body fluid, serum and the like also may be a measurement object of the measuring units 41 and 42. That is, the present invention is applicable to sample processing systems that include measuring units which measure urine or the likes, and the present invention is applicable to clinical sample processing systems that include measuring units which measure other types of clinical samples.

Figure 15A:
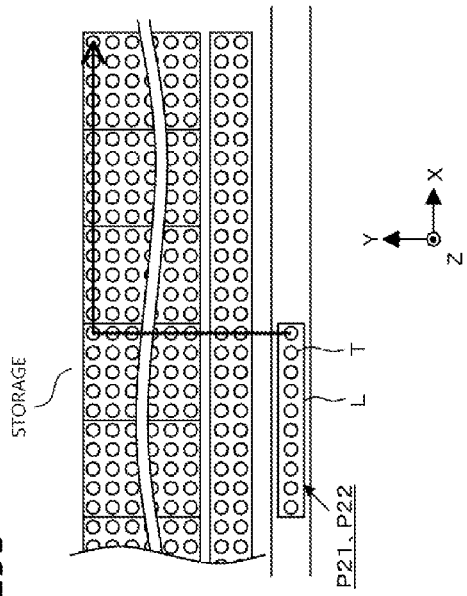
FIGS. 15A and 15B show the condition of the sample tube transfer in one embodiment.
Figure 15B:
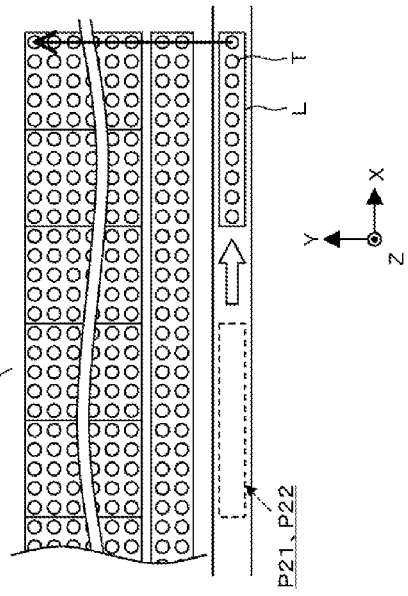

According to the above embodiment, the sample rack L disposed at position P21 is lifted up to position P22, and the transfer of the sample tube T is performed in this state as shown in FIG. 15A. In this configuration, if the target holder is far from the position P22 in the X-axis direction, the moving distance of the sample tube T in the X-axis direction increases as shown in FIG. 15B. To solve the problem, after the sample rack L is set at position P21, the rack may be moved in an oblique direction to approach the target holder of the storage 100. In this case, for example, the support member 131 of the lifting section 130 is inclined relative to the Z-axis direction within the XZ plane. As shown in FIG. 15D, the sample tubes T can be rapidly transferred compared to the above embodiment because the distances converge in the X-axis direction of the sample tube T to be transferred from the sample rack L and the holder of the storage.

Figure 16A:
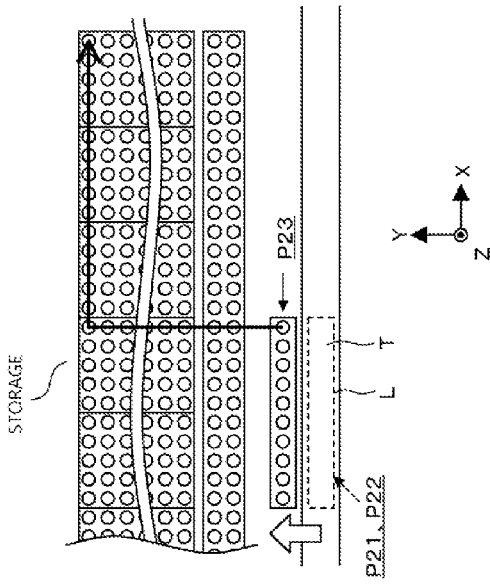
FIGS. 16A and 16B show the condition of the sample tube transfer in another modification.
Figure 16B:
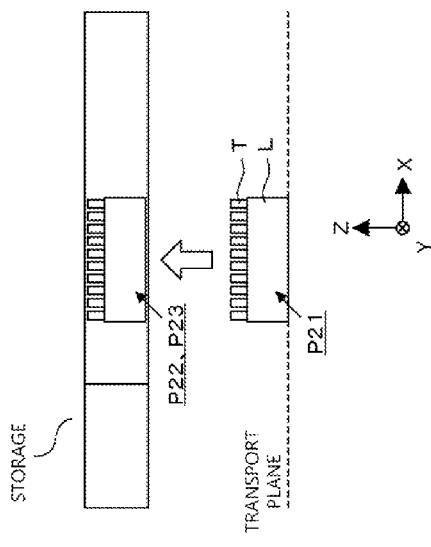

As shown in FIGS. 16A and B, the sample tube T also may be transferred when the sample rack L disposed at position P21 is moved slightly in an inclined direction toward position P23 on the Y-axis positive side of position P22. In this case, for example, the support member 131 of the lifting section 130 is inclined relative to the Z-axis direction within the YZ plane.

Note that "lifting up" is not limited to vertically lifting up the sample rack L disposed at position P21 to position P22 as in the above embodiment. That is, "lifting up" stated in the scope of the claims includes moving the sample rack L in an oblique direction within the XY plane as shown in FIGS. 15C and D, and moving the sample rack L in an oblique direction within the YZ plane as shown in FIGS. 16A and B.

Figure 15C:
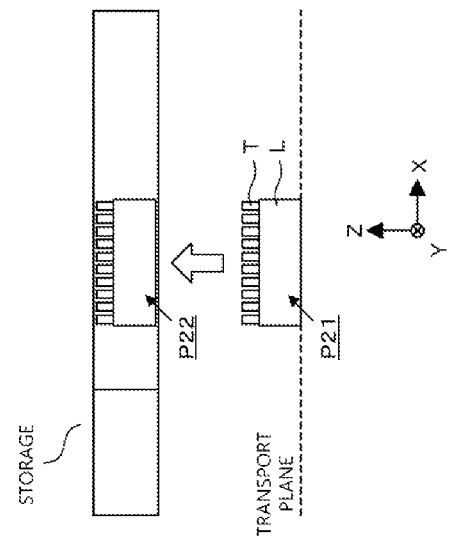
FIGS. 15C and 15D show the condition of the sample tube transfer in a modification.
Figure 15D:
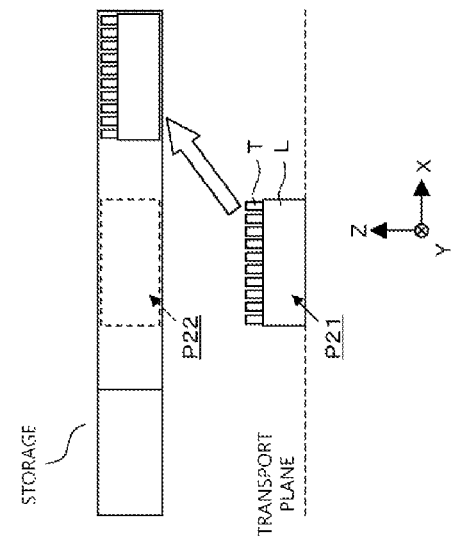

Although the sample rack L is moved in an oblique direction in FIGS. 15C and D, the sample rack L may be moved in the Z-axis direction and disposed at position P22, then moved in the X-axis direction. In FIGS. 16A and B, the sample rack L may be moved in the Z-axis direction and disposed at position P22, then moved in the Y-axis direction and disposed at position P23.

Figure 16C:
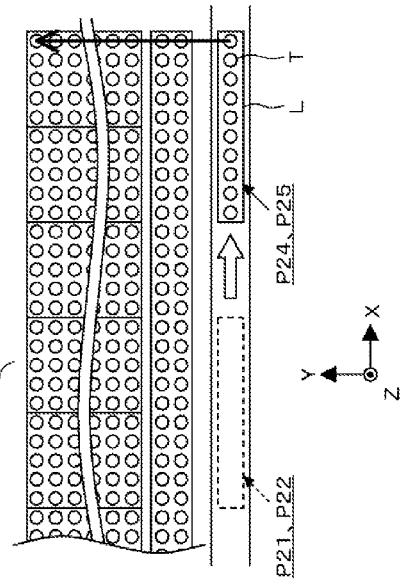
FIGS. 16C and 16D show the condition of the sample tube transfer in another modification.
Figure 16D:
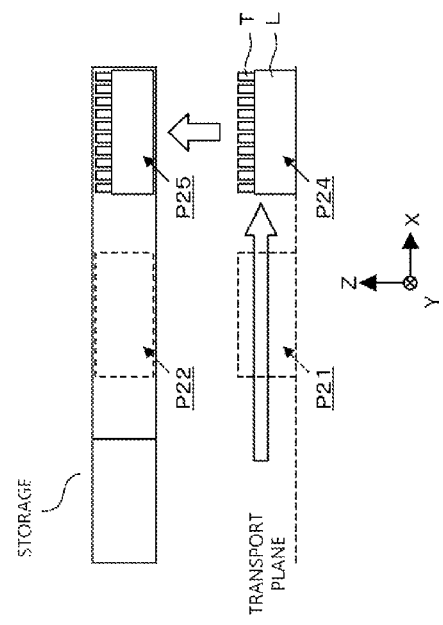

Although the lifting up of the sample rack L is only from position P21 to position P22 in the above embodiment, the present invention is not limited to this configuration inasmuch as the sample rack 1 also may be lifted up at another position on the transport path r1 in addition to the movement from position P21 to position P22. For example, a position P24 may be provided on the transport path r1 which is shifted in the X-axis direction relative to position P21 as shown in FIGS. 16C and D, such that the sample rack L disposed at position P24 can be lifted up and disposed at a position P25. In this case, the sample rack L is disposed at either position P22 and P25 so that the sample tube T to be transferred from the sample rack L and the holder of the target storage converge. Transferring the sample tube T is therefore rapidly performed compared to the above embodiment.

In the above embodiment, the sample rack L is disposed at position P22 so that the height of the bottoms of holding positions of the sample rack L are equal to the height of the bottom of holders of the storage 100 as shown in FIG. 10C. However, the present invention is not limited to this configuration. The sample rack L may be lifted to the level somewhat above or below the position P22. That is, the bottom heights of holding positions of the sample rack L are not necessarily same as the bottom heights of the holders of the storage 100. Even in this case, the sample tube T can be rapidly transferred compared to the mode illustrated with FIG. 10A.

When the sample rack L is disposed somewhat above position P22, it is preferable that a position P26 of the sample rack L after lifting is set so that the height H4 of the top surface of the sample rack L is approximately the same as the height H5 of the top surface of the cap T2 of the sample tube T held in the storage 100 as shown in FIG. 17A. In this way the vertical movement stroke of the sample tube T for sample transfer may be minimized so that the sample tube T held in the sample rack L is lifted up with a stroke only sufficient to remove the sample tube T from the sample rack L.

That is, under the configuration of position P26, the sample tube T is lifted up only a distance Z2 to be removed from the rack L so that the most bottom end of the sample tube T is somewhat higher than the height H4, and simultaneously the most bottom end of the sample tube T is positioned somewhat above the cap T2 of the sample tube T held in the storage 100 as shown in FIG. 17B. Thus, the sample tube T is moved in the Y-axis positive direction above the sample tube T held in the storage 100. Since Z2 is less than Z1 in this case, the vertical moving distance (Z2+Z1) required to transfer the sample tube T is smaller than the vertical moving distance (Z1+Z1) shown in FIG. 10C, that is, the vertical moving distance is minimized. Hence, the transfer of the sample tube T is performed most rapidly according to this configuration.

Note that when there is variation in the length of the sample tubes T handled in the tube sorter 22, the position P26 can be set according to the height of the top surface of the cap T2 of the longest sample tube T.

Although the two belts 111 and 112 are employed, and they are driven in linkage through the belt 115*a* in the above embodiment, a single belt 112 also may be used as shown in FIG. 17C. The configuration shown in FIG. 17C omits the belts 111 and 115*a* from the configuration shown in FIG. 15A, and adds pulleys 114*h* and 114*i* below the pulleys 113*b* and 114*a*. The belt 112 is looped around the pulleys 114*a* through 114*i*, and driven by the motor 116. In this case, a space S1 is created between the pulleys 113*b* and 114 and a space S2 is created between the pulleys 114*b* and 114*e* so that the supporting part 139 can be inserted in the spaces S1 and S2.

Although a single tube sorter is provided in the sample processing system 1 of the above embodiment as shown in FIG. 1, the present invention is not limited to this configuration inasmuch as two or more tube sorters may be installed adjacently.

Figure 18:
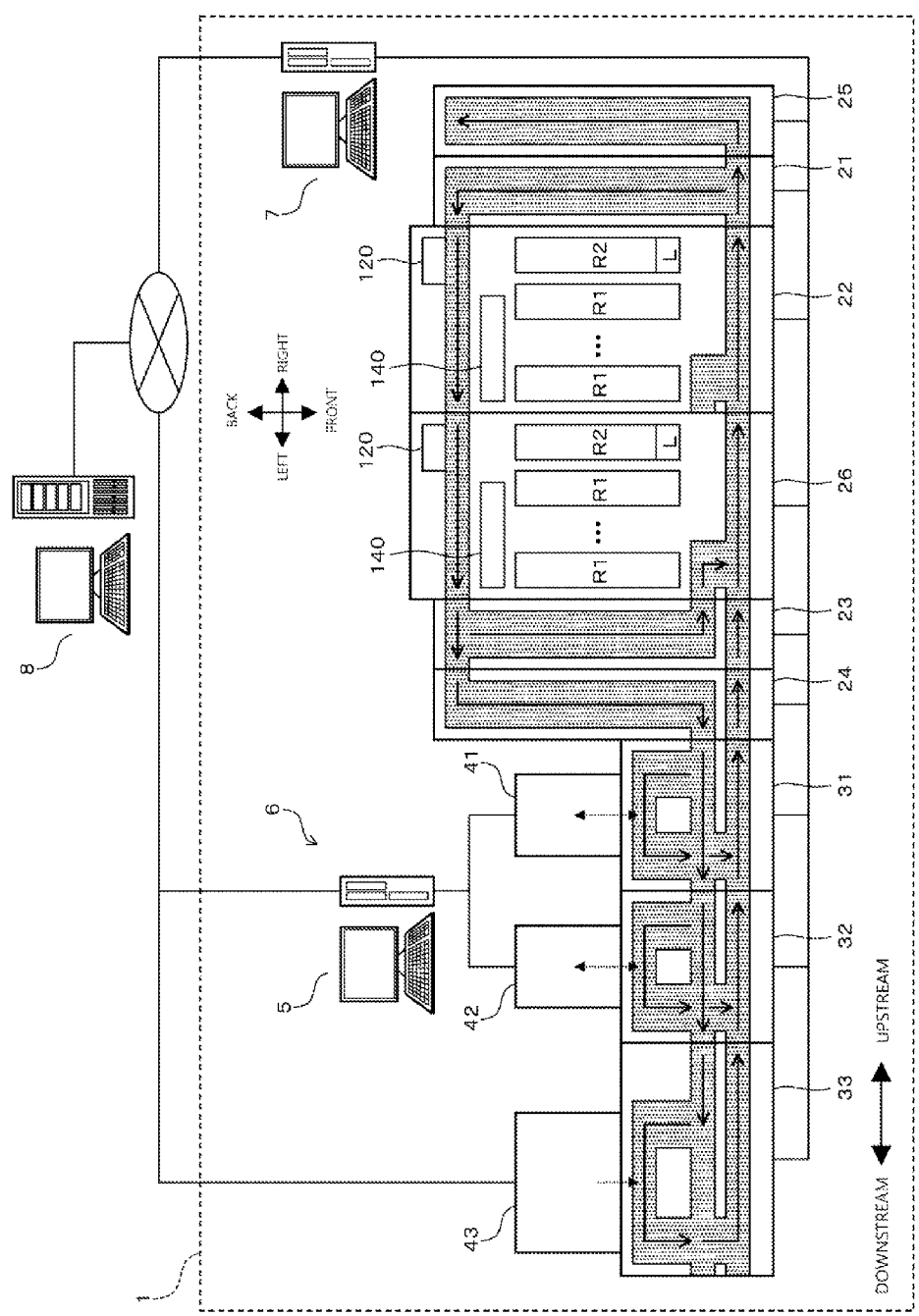
FIG. 18 shows the structure when viewing a modification of the sample processing system from above.

FIG. 18 shows an alternative of the sample processing system 1 employing two tube sorters. The sample processing system 1 shown in FIG. 18 has a tube sorter 26 installed between the tube sorter 22 and the relay unit 23 shown in FIG. 1. In this case, the sample rack L delivered to the downstream side from the receiving unit 21 is supplied to the two tube sorters 22 and 26, and the transfer of the sample tube T is performed.

In this case, when the transfer of the sample tube T is performed by the tube sorter 22, the sample rack L is lifted up by the supporting part 139 and the following sample rack L can be transported to the tube sorter 26. When the transfer of the sample tube T is performed by the tube sorter 26, the sample rack L is lifted up by the supporting part 139 and the following sample rack L can be transported to the relay unit 23. That is, the transport sequence of the sample racks L can be replaced without providing a separate transport path, and the next sample rack L can be moved downstream during the transfer of the sample tube T. Hence, the transfer of the sample tube T can be performed rapidly.

Figure 19:
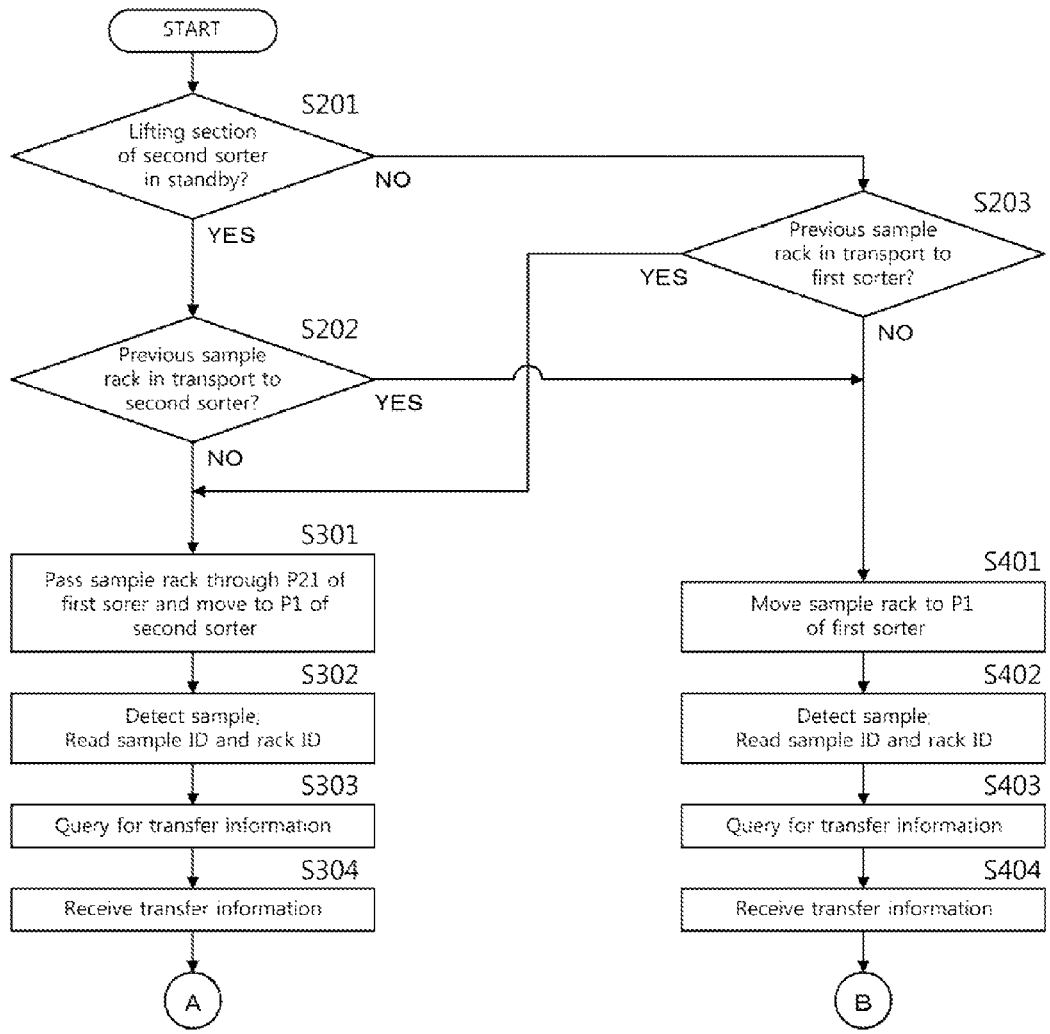
FIG. 19 is a flow chart (first half) showing the operation of the sample processing system of the modification.
Figure 20:
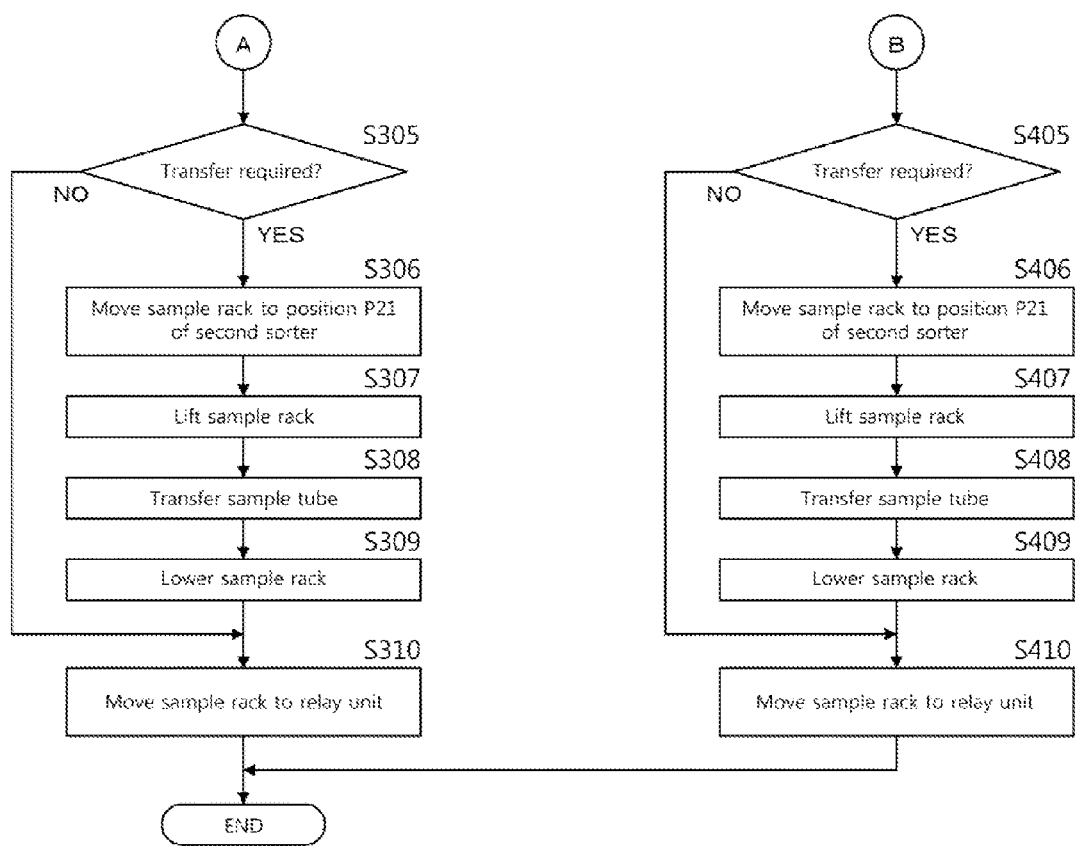
FIG. 20 is a continuation of FIG. 19.

FIGS. 19 and 20 are flow charts showing the process performed by the system which includes two tube sorters. This process starts when the sample rack L at the back of the receiving unit 21 is positioned. In the process shown in FIGS. 19 and 20, tube sorters 22 and 26 are respectively referred to as the "first tube sorter" and the "second tube sorter". And hereinafter the sample rack L presents at the back of the receiving unit 21 is referred to as "target rack".

Referring to FIG. 19, a controller 701 of the transport controller 7 determines whether the lifting section 130 of the second tube sorter 26 is on standby, that is, whether the supporting part 139 of the lifting section 130 on standby state as shown in FIG. 9A, and whether a sample rack L is disposed at position P21 (S201). This determination is performed based on the drive position of the motor 136 of the lifting section 130 and the detection signal of the sensor s2.

The controller 701 then determines whether previous rack L which has been delivered downstream from the receiving unit 21, that is, the sample rack L transported immediately before the target rack L, is being transported to the first tube sorter 22 or being transported to the second tube sorter 26 (S202, S203). This determination is performed based on the history of transport instructions stored on the hard disk 703 of the transport controller 7, and the detection signals of the sensors s1 through s3 of the first and second tube sorters 22 and 26.

When the lifting section 130 of the second tube sorter 26 is on standby (S201: YES) and the immediately previous rack L is not being transported to the second tube sorter 26 (S202: NO), the controller 701 transmits instructions to the first tube sorter 22 and second tube sorter 26 to perform transfer on the target rack L by the second tube sorter 26. Thereafter, the target rack L is moved from the receiving unit 21 to the first tube sorter 22, and the process advances to S301. When the lifting section 130 of the second tube sorter is not on standby (S201: NO) and the immediately preceding rack L is being transported to the first tube sorter 22 (S203: YES), the process similarly advances to S301.

When the lifting section 130 of the second tube sorter 26 is not on standby (S201: NO) and the immediately preceding rack L is not being transported to the first tube sorter 22 (S203: NO), the controller 701 transmits instructions to the first tube sorter 22 and second tube sorter 26 to perform transfer on the target rack L by the first tube sorter 22. Thereafter, the target rack L is moved from the receiving unit 21 to the first tube sorter 22, and the process advances to S401. When the lifting section 130 of the second tube sorter 26 is on standby (S201: YES) and the immediately preceding rack L is being transported to the second tube sorter 26 (S202: YES), the process similarly advances to S401.

Figure 21:
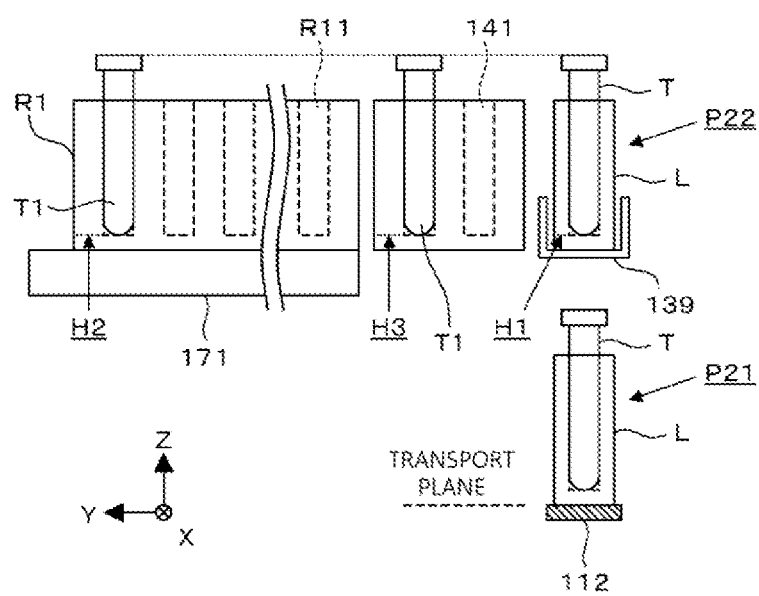
FIG. 21 shows the condition of a second rack passing beneath a rack lifted up in a lift state.

When the target rack L is determined to be processed by the second tube sorter 26, the target rack L delivered from the receiving unit 21 passes through the position P22 of the first tube sorter 22 and is delivered to the second tube sorter 26 by the controller 321 of the first tube sorter 22. Then, when the supporting part 139 of the first tube sorter 22 is in the standby state as shown in FIG. 9A, the target rack L passes over the supporting part 139 and passes through the position P21 as shown in FIG. 9B. When the supporting part 139 of the first tube sorter 22 is in the lift state as shown in FIG. 9C, the sample rack L passes under the supporting part 139 and passes through the position P21 as shown in FIG. 21. The sample rack L is then moved to position P1 in the second tube sorter 26 by the controller 321 of the second tube sorter 26 (S301).

The controller 321 of the second tube sorter 26 then detects whether a sample tube T is held at holding positions on the target rack L, and reads the sample ID and the rack ID via the barcode unit 120 (S302). The controller 321 of the second tube sorter 26 then queries the host computer 8 for transfer information for the held sample tubes T (S303). Thereafter, the controller 321 of the second tube sorter 26 receives the transfer information for all sample tubes T queried in S303 (S304).

Next, referring to FIG. 12, the controller 321 of the second tube sorter 26 determines whether any sample tube T must be transferred to/from the target rack L based on the transfer information received in S304 (S305). When no sample tube T requires transfer (S305: NO), the controller 321 of the second tube sorter 26 controls the transport section 110 to transport the target rack L in a leftward direction from position P1, passing through the position P21 of the second tube sorter 26 and delivers the target rack L to the relay unit 24 (S310). The target rack L waits at position P1 of the second tube sorter 26 when the supporting part 139 is not in the standby state or lift state. The target rack L passes through the position P21 after the supporting part 139 becomes in the standby state or lift state.

When a sample tube T requires transfer (S305: YES), the controller 321 of the second tube sorter 26 controls the transport section 110 to transport the target rack L in a leftward direction from position P1 to position P21 (S306). Then, the controller 321 of the second tube sorter 26 controls the lifting section 130 to lift up the target rack L disposed at position P21 with the supporting part 139, and places the target rack L at position P22 (S307). The controller 321 of the second tube sorter 26 then controls the tube transferring section 200 to transfer the sample tube T requiring transfer to/from the sample rack L (S308).

When the transfer of the sample tube T is completed, the controller 321 of the second tube sorter 26 controls the lifting section 130 to lower the target rack L from position P22 to position P21 (S309). Then the controller 321 of the second tube sorter 26 controls the transport section 110 to transport the target rack L from position P21 to the relay unit 24 (S310). Processing of the sample rack L by the second tube sorter is thus completed.

Referring to FIG. 19, when the target rack L is determined to be processed by the first tube sorter 22, the target rack L delivered from the receiving unit 21 is moved to position P1 of the first tube sorter 22 (S401). The controller 321 of the first tube sorter 22 then detects whether a sample tube T is held at holding positions on the target rack L, and reads the sample ID and the rack ID via the barcode unit 120 (S402). The controller 321 of the first tube sorter 22 then queries the host computer 8 for transfer information for the held sample tubes T (S403). Thereafter, the controller 321 of the first tube sorter 22 receives the transfer information for all sample tubes T queried in S403 (S404).

Next, referring to FIG. 20, the controller 321 of the first tube sorter 22 determines whether any sample tube T must be transferred to/from the target rack L based on the transfer information received in S404 (S405). When no sample tube T requires transfer (S405: NO), the controller 321 of the first tube sorter 22 controls the transport section 110 to transport the target rack L in a leftward direction from position P1, passing through the position P21 and delivers the target rack L to the relay unit 24 (S410). The sample rack L waits at position P1 of the first and second tube sorters 22 and 26 when the supporting part 139 is not in the standby state or lift state. The target rack L passes through the position P21 of the first and second tube sorters 22 and 26 after the supporting part 139 becomes in the standby state or lift state.

When a sample tube T requires transfer (S405: YES), the controller 321 of the first tube sorter 22 controls the transport section 110 to transport the target rack L in a leftward direction from position P1 to position P21 (S406). Then, the controller 321 of the first tube sorter 22 controls the lifting section 130 to lift up the target rack L disposed at position P21 via the supporting part 139, and places the sample rack L at position P22 (S407). The controller 321 of the first tube sorter 22 then controls the tube transferring section 200 to transfer the sample tube T requiring transfer to/from the target rack L (S408).

When the transfer of the sample tube T is completed, the controller 321 of the first tube sorter 22 controls the lifting section 130 to lower the target rack L from position P22 to position P21 (S409). The controller 321 of the first tube sorter 22 controls the transport section 110 to transport the target rack L in a leftward direction from position P21, passing through the position P21 of the second tube sorter 26 and delivers the target rack L to the relay unit 24 (S410). Processing of the target rack L by the first tube sorter 22 is thus completed.

Although the above embodiment is configured so that the top surface side and bottom surface side of the rack regulating member F is symmetrical relative to the XY plane, the present invention is not limited to this configuration inasmuch as the inclined surfaces F12, F22, and F32 of the top side may be omitted as shown in FIG. 11A. In this case, the rack regulating member installed on the right side is a member with a symmetrical shape on the YZ plane relative to the rack regulating member F shown in FIG. 22A because the rack regulating members installed on the right and left sides do not have the same shape.

Figure 22B:
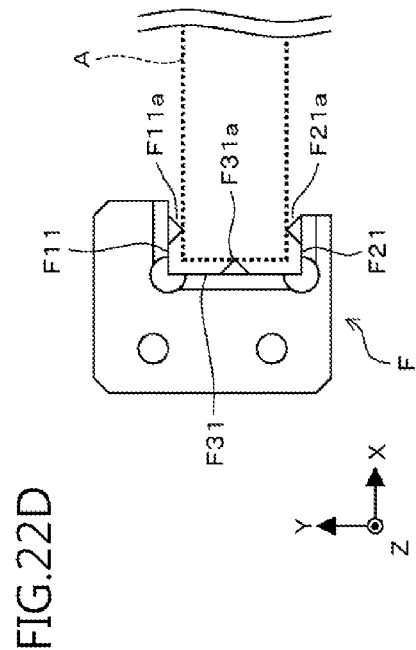
FIGS. 22A through 22D show modifications of the rack regulating member.
Figure 22A:

Although the above embodiment stipulates region A by surfaces F11, F21, and F31, the present invention is not limited to this stipulation inasmuch as the stipulation may be made by lines. For example, surfaces F11, F21, and F31 may be omitted and the inclined surfaces F12, F22, and F32 on the top and bottom sides may be connected in the rack regulating member F as shown in FIG. 22B. In this case, region A may be stipulated by the ridge line between the top and bottom sides of the inclined surface F12, the ridge line of the top and bottom sides of the inclined surface F22, and the ridge line of the top and bottom sides of the inclined surface F32.

Figure 22D:
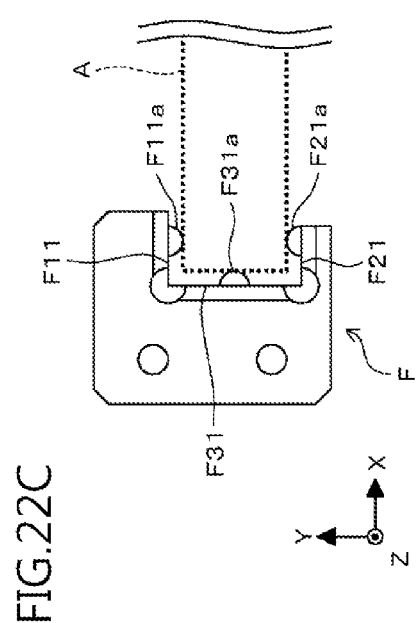
Figure 22C:
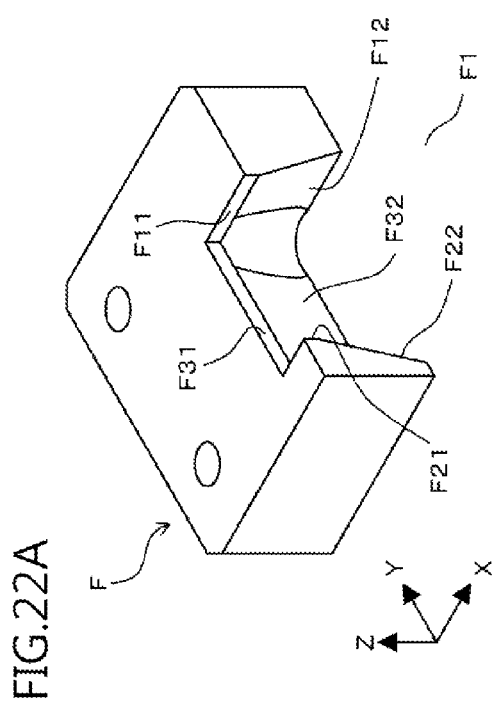

Region A also may be stipulated by points. For example, hemispherical projections F11a, F21a, and F31a may be provided on surfaces F11, F21, and F31 in the rack regulating member F as shown in FIG. 22C. The projections F11a, F21a, and F31a also may be conical in shape as shown in FIG. 22D. In the cases shown in FIGS. 22C and 22D, region A is stipulated by the points of the tips of the projections F11a, F21a, and F31a.

Figure 23A:
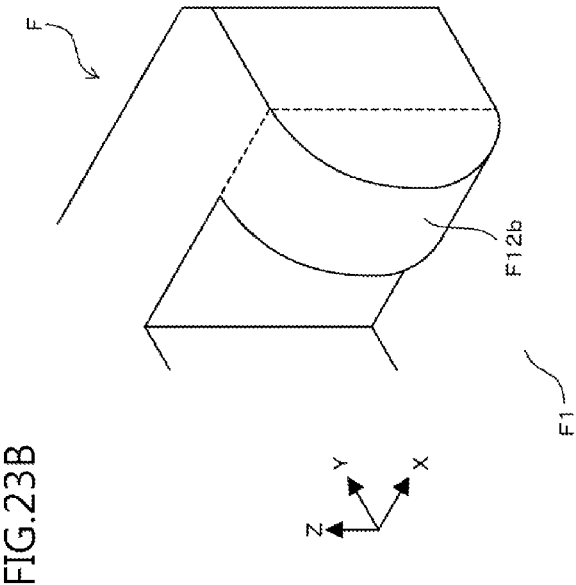
FIGS. 23A through 23D show modifications of the rack regulating member.

Although the lifted sample rack L is guided to position P22 by the inclined surfaces F12, F22, and F32 in the above embodiment, the present invention is not limited to this configuration inasmuch as the sample rack L also may be guided by another guiding means. For example, two inclined surfaces F12 may be formed one step lower, and two projections F12a may respectively extend in the incline direction on the two inclined surfaces F12 in the rack regulating member F as shown in FIG. 23A. Note that the inclined surfaces F22 and F32 may have similar projections (not shown in the drawing). In this case, the sample rack L is guided to the position P22 along the tips of the projections provided on the inclined surfaces F12, F22, and F32.

Figure 23B:
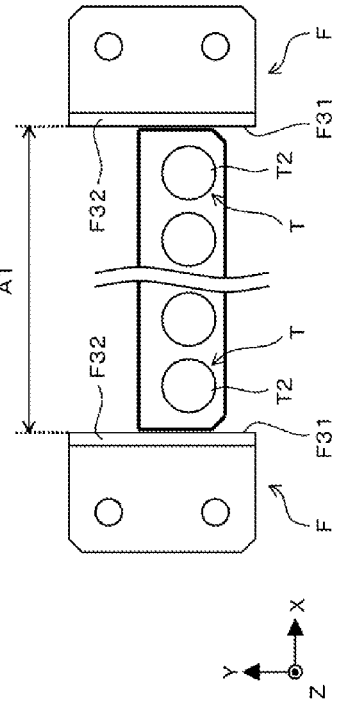

Guidance by flat surfaces such as the inclined surfaces F12, F22, and F32 is not necessary inasmuch the lifted sample rack L also may be guided via a curved surface. For example, a half cylinder part F12b also may be provided on the interior wall surface of the opening F1 in place of the surface F11 and two inclined surfaces F12 in the rack regulating member F as shown in FIG. 23B. Note that surface F21 and two inclined surfaces F22, and surface F31 and two inclined surfaces F32 similarly may be provided with half cylinder projections (not shown in the drawing) in place of the aforesaid. In this case, the sample rack L is guided to the position P22 along the curvature of the cylindrical part. The sample rack L also may be positioned by sandwiching the sample rack L via the apexes of the mutually opposed cylindrical parts F12b to regulate movement of the sample rack L.

Although movement of the sample rack L disposed at position P22 is regulated in both the X-axis direction and Y-axis direction via the rack regulating member F in the above embodiment, the present invention is not limited to this mode of regulation inasmuch as movement of the sample rack L in either the X-axis direction or Y-axis direction may be regulated.

Figure 23C:
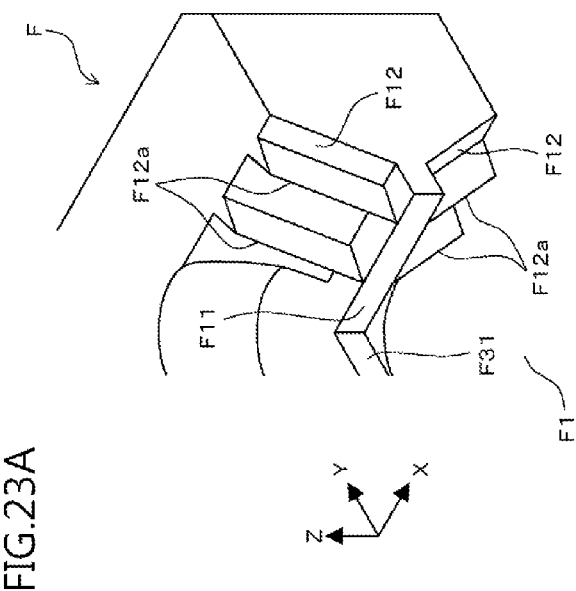
Figure 23D:
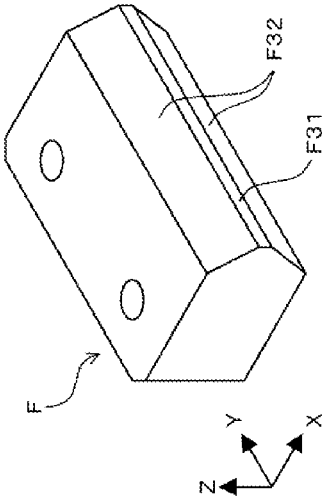

FIG. 23C shows the structure of a rack regulating member F for regulating only the movement of the sample rack L in the X-axis direction (longitudinal direction). In this case the rack regulating member F has a shape which omits surfaces F11 and F21 and inclined surfaces F12 and F22 from the rack regulating member F of the above embodiment shown in FIG. 14A. In this case, as shown in FIG. 23D, the sample rack L is positioned within the region A set by the two surfaces F31 when the rack is lifted and movement is regulated in the X-axis direction in the lift state even when the sample rack L shifts from position P21 in the X-axis direction in the transport plane. Note that movement of the sample rack L in the Y-axis direction (lateral direction) is roughly regulated by the supporting part 139 (refer to FIG. 8) of the lifting section 130. The sample rack L is thus placed at position P22 and movement within the XY plane is regulated in the lift state similar to the above embodiment.

Although movement of the sample rack L disposed at position P22 is regulated in the XY plane by the rack regulating member F in the above embodiment, the flat spring 182 described below also may be used to regulate the movement in the Z-axis positive direction of the sample rack L disposed at position P22.

FIG. 24A shows the structure of a flat spring 182 provided on the rack regulating member F. The two flay springs 182 are fixedly attached to the top surface of the left and right rack regulating members F. The two flat springs 182 are configured of metal and have mutually identical shapes. In the state shown in FIG. 24A, the two flat springs 182 are installed reversed front and back, and are mutually symmetrical in the YZ plane. When viewed from the top (Z-axis negative direction) as shown in FIGS. 24B and 24C, the flat springs 182 are configured encompass one part of the sample rack 1 disposed at position P22.

When the flat spring 182 is configured in this way and arranged on the top surface of the rack regulating member F, lifting up of the sample rack L is suppressed by the removal of the sample tube T from the sample rack L when a sample tube T held in the sample rack L is drawn from the sample rack L by the gripper 243. Damage to the sample tube T caused by collision of the lifted sample rack L falling on the supporting part 139 is therefore prevented. Abnormal transport of the sample rack L is also avoided by stopping the sample rack L in this state.

In this case, the sample rack L is accurately set at the position P22 and damage to the flat springs 182 even when the lifted sample rack L collides with the flat springs 182 since the flat springs 182 are configured of metal.

Note that in this case the top surface of the sample rack L is pressed by the flat springs 182 when the step motor 136 of the lifting section 130 is regulated to lift the supporting part 139 of the lifting section 130. In this instance pressing down on the sample rack L due to withdrawing the sample tube T from the sample rack L is prevented when the sample tube T is set in the sample rack L at position P22. Damage to the sample tube T is prevented when the depressed sample rack L collides upon returns to position P22. Abnormal transport of the sample rack L is also avoided by stopping the depressed sample rack L in this state.

Note that the present invention is not limited to the above described embodiments and may be variously modified insofar as such modification are within the scope of the claims.

What is claimed is:

1. A tube sorter comprising:
   a transporting section configured to transport a sample rack along a transport path;
   a storage arranged at a higher level than the transporting section, capable of storing a plurality of sample tubes;
   a lifting section configured to lift up the sample rack transported by the rack transporting section from a first position in the transport path to a second position directly above the transport path; and
   a sample tube transferring section configured to remove a sample tube from the sample rack at the second position lifted up by the lifting section without moving the sample rack from the second position and set the removed sample tube in the storage without moving the sample rack from the second position.

2. The tube sorter of claim 1, wherein the lifting section lifts the sample rack upward vertically from the rack transporting section.

3. The tube sorter of claim 1, wherein the lifting section lifts the sample rack to a predetermined height and maintains the height until lowering the sample rack, without moving the sample rack to above the storage.

4. The tube sorter of claim 1, wherein
   the sample tube transferring section includes a gripper driven by a drive section; and
   the gripper is driven by the drive section so as to remove the sample tube from the sample rack lifted up by the lifting section and set the removed sample tube in the storage by:
   gripping the sample tube in the sample rack lifted by the lifting section;
   moving upward to remove the gripped sample tube;
   moving the gripped sample tube to above the storage; and
   lower the gripped sample tube to set the gripped sample tube in a target holder of the storage.

5. The tube sorter of claim 1, wherein the lifting section lifts the sample rack to a height at which the sample tube held in the sample rack is approximately the same height as the sample tube held in the storage.

6. The tube sorter of claim 5, wherein the lifting section lifts the sample rack so that a height of a bottom of a holding position of the sample rack is substantially the same as a bottom of a holder of the storage.

7. The tube sorter of claim 1, wherein
   the transporting section includes a belt extending along the transport path; and
   the lifting section includes a supporting part configured to support a bottom of the sample rack, and a drive unit configured to move the supporting part up and down between an upper end and a lower end;
   wherein the transporting section is configured to transport the sample rack by the belt over the supporting part when the supporting part is at the lower end.

8. The tube sorter of claim 1, further comprising:
   an identification information obtaining section for acquiring identification information from the sample tubes held in the sample rack being transported by the transporting section;
   wherein the lifting section lifts the sample rack and the tube transferring section removes the sample tube from the sample rack and sets the sample tube in the storage when the sample tube is determined to be sorted based on the identification information acquired by the identification information obtaining section.

9. The tube sorter of claim 1, wherein
   when transferring the sample tube from the storage to the sample rack,
   the lifting section lifts the sample rack,
   the tube transferring section removes the sample tube from the storage and sets the removed sample tube in the sample rack lifted by the lifting section.

10. The tube sorter of claim 1, wherein
    the transport path includes a first transport path provided with the lifting section at the first position, and a second transport path which is different than the first transport path;
    the storage is arranged above the second transport path.

11. The tube sorter of claim 10, wherein
the storage is divided into multiple sections, and
each of the sections of the storage is configured to be drawn separately in the forward direction.

12. The tube sorter of claim 10, wherein
the storage includes a plurality of holders each configured to receive the sample tube;
the tube transferring section is configured to set the sample tubes so as to sequentially fill the holders from one nearest the second transport path.

13. The tube sorter of claim 1, further comprising:
a regulating member disposed above the rack transporting section to regulate a horizontal movement of the sample rack lifted by the lifting section,
wherein the lifting section lifts the sample rack to dispose the sample rack within a regulating region defined by the regulating member.

14. The tube sorter of claim 13, wherein
the regulating member has a guide part which abuts the sample rack and guides the sample rack to the regulating region when the sample rack is lifted by the lifting section.

15. The tube sorter of claim 1, further comprising:
a regulating member disposed above the rack transporting section to regulate a movement of the sample rack lifted by the lifting section, the regulating member regulating the movement of the sample rack in an X-axis direction.

16. The tube sorter of claim 13, wherein
the lifting section is configured to support a bottom of the sample rack and to lift the supported sample rack, and
the regulating member is arranged so as to be abutted with an upper part of the sample rack lifted by the lifting section.

17. The tube sorter of claim 13, wherein
the regulating member includes a frame having an opening through which the sample rack passes when the sample rack is lifted by the lifting section.

18. The tube sorter of claim 13, wherein
the regulating member includes a member which regulates an upward movement of the sample rack lifted by the lifting section.

19. A tube sorting system comprising:
the tube sorter of claim 1 as a first tube sorter;
a second tube sorter arranged adjacently to the first tube sorter, the second tube sorter comprising at least:
a transporting section configured to transport a sample rack delivered from the first tube sorter;
a storage capable of storing a plurality of sample tubes; and
a sample tube transferring section configured to remove a sample tube from the sample rack and set the removed sample tube in the storage; and
a controller programmed to control the first tube sorter to pass through a first sample rack by the transporting section while the lifting section of the first tube sorter is lifting a second sample rack and to deliver the first sample rack to the second tube sorter.

* * * * *